(12) United States Patent
Prasannakumar et al.

(10) Patent No.: US 8,989,872 B2
(45) Date of Patent: Mar. 24, 2015

(54) IMPLANTABLE MEDICAL DEVICE HEADER

(71) Applicant: Medtronic, Inc., Minneapolis, MN (US)

(72) Inventors: Jeevan M. Prasannakumar, Circle Pines, MN (US); Christopher M. Haenisch, Fridley, MN (US); David Bates, Plymouth, MN (US); John C. Olson, Coon Rapids, MN (US); George Patras, Greenfield, MN (US); Yanzhu Zhao, Blaine, MN (US); Jason P. Weiand, Rockford, MN (US)

(73) Assignee: Medtronic, Inc., Minneapolis, MN (US)

( * ) Notice: Subject to any disclaimer, the term of this patent is extended or adjusted under 35 U.S.C. 154(b) by 24 days.

(21) Appl. No.: 13/676,839

(22) Filed: Nov. 14, 2012

(65) Prior Publication Data
US 2014/0135882 A1   May 15, 2014

(51) Int. Cl.
*A61N 1/05* (2006.01)
*A61N 1/375* (2006.01)

(52) U.S. Cl.
CPC ............... *A61N 1/05* (2013.01); *A61N 1/3752* (2013.01)
USPC .......................................................... 607/119

(58) Field of Classification Search
CPC ............................. A61N 1/375; A61N 1/3752
USPC ........................................... 607/36, 115–119
See application file for complete search history.

(56) References Cited

U.S. PATENT DOCUMENTS

| | | | |
|---|---|---|---|
| 5,851,221 A | 12/1998 | Rieder et al. | |
| 5,871,514 A * | 2/1999 | Wiklund et al. | 607/36 |
| 6,152,761 A | 11/2000 | Wellinsky et al. | |
| 6,601,296 B1 | 8/2003 | Dailey et al. | |
| 6,817,905 B2 | 11/2004 | Zart et al. | |
| 7,274,963 B2 | 9/2007 | Spadgenske | |
| 7,489,968 B1 | 2/2009 | Alexander et al. | |
| 7,654,843 B2 | 2/2010 | Olson et al. | |
| 7,988,497 B2 | 8/2011 | Ries et al. | |
| 2002/0107555 A1 | 8/2002 | Rusin et al. | |
| 2004/0215280 A1 | 10/2004 | Dublin et al. | |
| 2008/0303728 A1 | 12/2008 | Lee et al. | |
| 2009/0093855 A1 | 4/2009 | Mueller et al. | |
| 2009/0270961 A1 * | 10/2009 | Ruschel et al. | 607/119 |
| 2010/0019985 A1 | 1/2010 | Bashyam et al. | |
| 2011/0015694 A1 * | 1/2011 | Alexander et al. | 607/36 |
| 2012/0001812 A1 | 1/2012 | Zhao et al. | |
| 2012/0123497 A1 | 5/2012 | Sherva et al. | |

OTHER PUBLICATIONS (PCT US2013/066084) PCT Notification of Transmittal of the International Search Report and the Written Opinion of the International Searching Authority, Mailed Dec. 20, 2013, 6 pages.

\* cited by examiner

*Primary Examiner* — Rex R Holmes

(57) ABSTRACT

Techniques for forming a header for an implantable medical device via a two-shot molding process are described. The two-shot molding processes may include a first molding step that creates a first-shot assembly and a second molding step that creates a second-shot assembly. The first-shot assembly may be formed to include one or more protrusions configured to interact with a second-shot mold and/or molding material in the second molding step. The second molding step may be configured to overmold the first-shot assembly. The header may include an attachment plate at least partially embedded in molding material and configured to be mechanically coupled to a body of the implantable medical device.

20 Claims, 21 Drawing Sheets

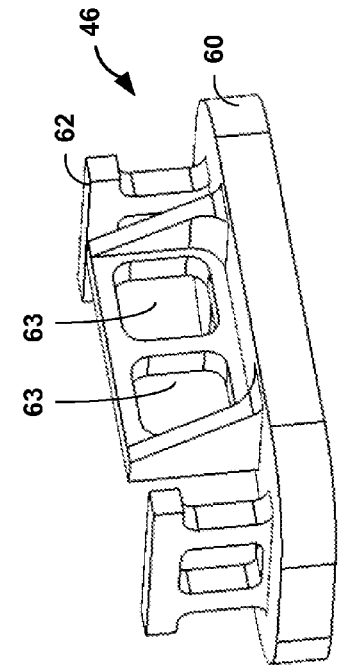
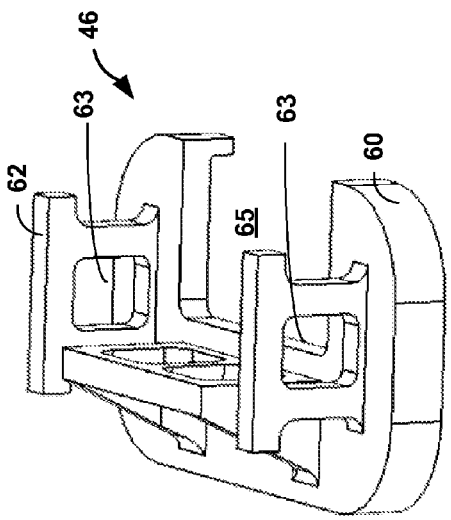
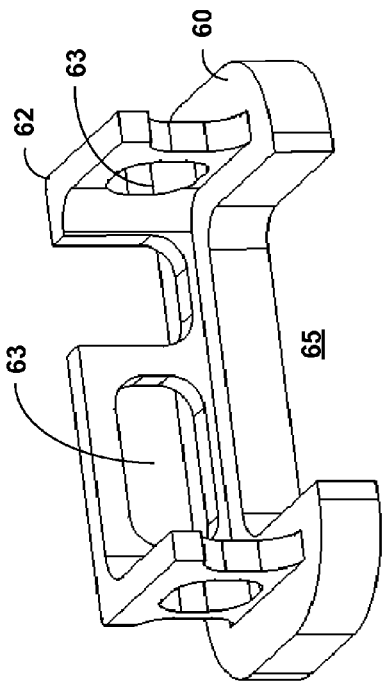
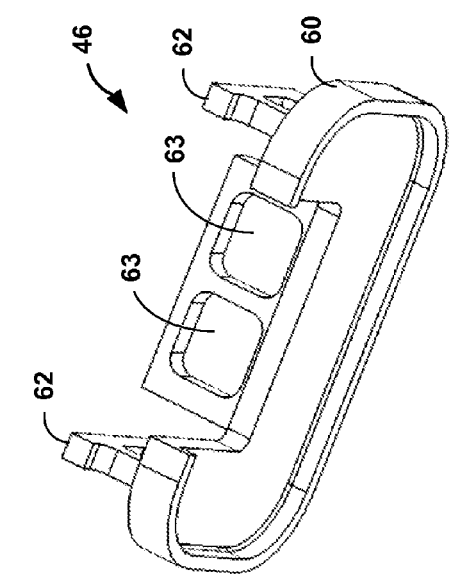

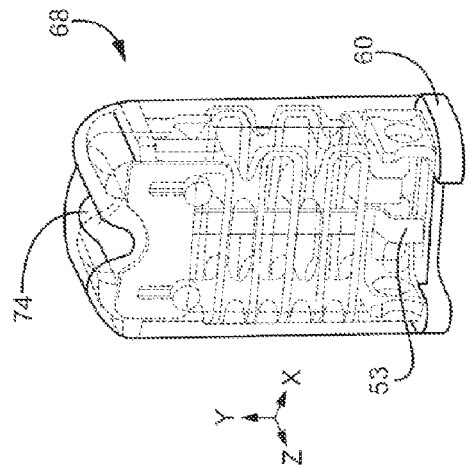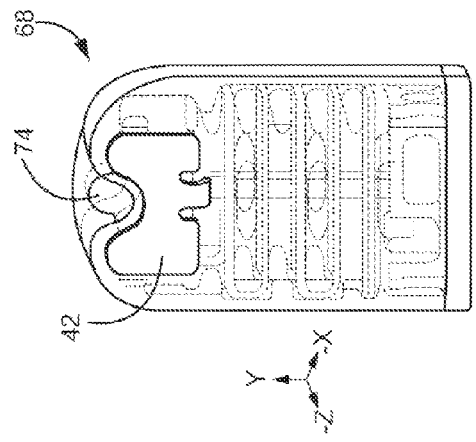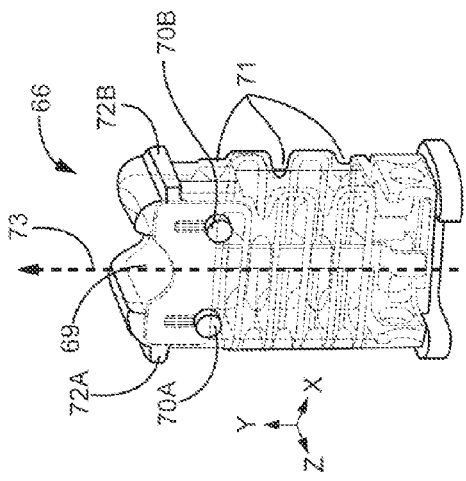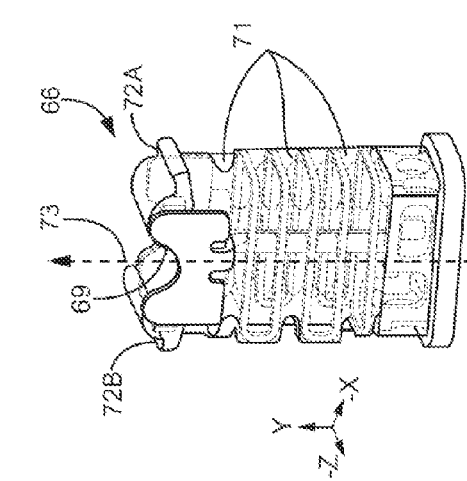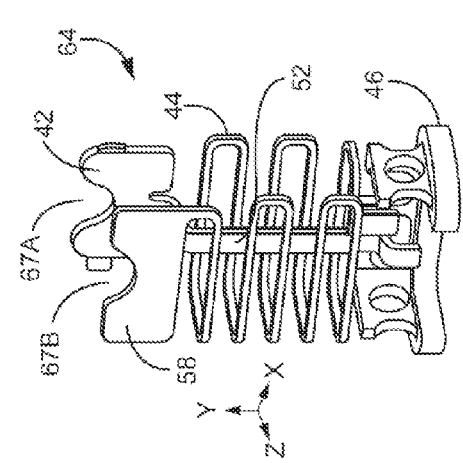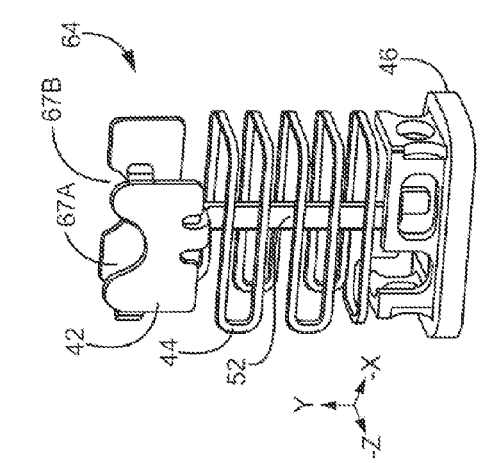

IMPLANTABLE MEDICAL DEVICE HEADER

TECHNICAL FIELD

The disclosure relates to implantable medical devices and, in particular, to headers for implantable medical devices.

BACKGROUND

Implantable medical devices (IMDs) may be configured to provide one or more therapies to a patient. For example, an IMD may be implantable within the body of a patient to deliver electrical stimulation therapy such as cardiac stimulation therapy or neurostimulation therapy. An example of cardiac stimulation therapy is cardiac pacing, which may include bradycardia pacing, antitachycardia pacing, or cardiac resynchronization therapy. An IMD may that delivers cardiac stimulation therapy may also provide cardioversion or defibrillation. Examples of neurostimulation therapy include spinal cord stimulation, deep brain stimulation, gastric stimulation, peripheral nerve stimulation, or pelvic floor stimulation. In other examples, an IMD may be configured to deliver drug therapy to a patient.

In addition to, or instead of delivering therapy, an IMD may be configured to sense one or more physiological parameters of a patient. For example, an IMD may be configured to sense various electrical signals of a patient, such as a cardiac electrogram signal, an electroencephalogram or other brain signal, or an electromyogram signal. As other examples, an IMD may be configured to sense a cardiovascular or cerebral spinal fluid pressure or flow, heart sounds, patient movement or posture, temperature, blood oxygen saturation, respiration, edema, or pH.

In some examples, an IMD may include a hermetically sealed housing that encloses internal circuitry such as a hybrid circuit board and one or more batteries. The IMD may also include a header portion, referred to as a header, which may include an insulating block configured to isolate one or more conductors from each other and the surrounding environment. The header portion may be configured to house one or more components of the IMD, such as an antenna or electrode.

SUMMARY

In general, the disclosure is directed to techniques for forming a header for an implantable medical device via a two-shot molding process. Molding processes described herein may include a first molding step that creates a first-shot assembly and a second molding step that creates a second-shot assembly. The second molding step may be configured to overmold the first-shot assembly. In some examples, the first-shot assembly may be formed to include one or more features configured to interact with a mold or a molding material in the second molding step. For example, the first-shot assembly may include one or more protrusions created by one or more divots of the first-shot mold, and the one or more protrusions may be particularly configured to perform specific functions during the second molding step. The header may also include an attachment plate at least partially embedded in molding material and configured to be mechanically coupled to a body of the implantable medical device.

In one example, the disclosure is directed a method of forming a header for an implantable medical device, the method comprising positioning a pre-molding assembly within a first-shot mold, wherein the pre-molding assembly comprises an antenna, an electrode, and an attachment plate, and wherein the first-shot mold defines at least one divot; and creating a first-shot assembly by introducing a first shot molding material into the first-shot mold, wherein the first-shot assembly comprises the pre-molding assembly at least partially covered by the first-shot molding material, wherein the first-shot assembly comprises at least one protrusion of the first shot molding material extending from a surface of the first-shot assembly and formed by introduction of the first shot molding material into the at least one divot of the first-shot mold.

In another example, the disclosure is directed to a header for an implantable medical device, the header comprising a first-shot assembly comprising a pre-molding assembly at least partially covered by a molding material, wherein the pre-molding assembly comprises an antenna, an electrode, and an attachment plate, wherein the first-shot assembly comprises at least one protrusion of the first shot molding material extending from a surface of the first-shot assembly and formed by introduction of the first shot molding material into the at least one divot of the first-shot mold.

In another example, the disclosure is directed a header for an implantable medical device, the header comprising a header body comprising molding material and at least one component within the molding material; and an attachment plate configured to couple the header to a body of the implantable medical device, wherein the attachment plate comprises a base configured to be mechanically coupled to the body of the implantable medical device, wherein the base defines a space configured to receive at least one feedthrough wire from the body of the implantable medical device, the at least one feedthrough wire configured to be coupled to the at least one component of the header body; and at least one extension extending from the base of the attachment plate, wherein the at least one extension defines at least one void configured to receive a portion of the molding material to couple the attachment plate to the header body.

In another example, the disclosure is directed to an implantable medical device comprising a header comprising a header body comprising molding material and at least one component within the molding material, and an attachment plate comprising a base that defines a space, and at least one extension extending from the base, wherein the at least one extension defines at least one void configured to receive a portion of the molding material to mechanically couple the attachment plate to the header body, wherein the at least one extension is substantially embedded in the molding material; a body comprising electrical circuitry; and a feedthrough wire positioned through the space defined by the base of the attachment plate, wherein the feedthrough wire electrically couples the electrical circuitry and the at least one component of the header body, and wherein the base of the attachment plate is mechanically coupled to the body of the implantable medical device.

In another example, the disclosure is directed to a method comprising forming a header for an implantable medical device, wherein the header comprises a header body comprising molding material and at least one component within the molding material, and an attachment plate comprising a base that defines a space, and at least one extension extending from the base, wherein the at least one extension defines at least one void configured to receive a portion of the molding material to mechanically couple the attachment plate to the header body, wherein the at least one extension is substantially embedded in the molding material; positioning at least one feedthrough wire through the space defined by the base of the attachment plate; electrically coupling the at least one feedthrough wire to the component of the header; and mechanically coupling the base of the attachment plate to the body of the implantable medical device, wherein the at least one feedthrough wire is configured to electrically couple electrical circuitry of the body of the implantable medical device to the component of the header.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIGS. 5A-5D are schematic diagrams illustrating an attachment plate of a header for an IMD.

FIGS. 6A and 6B illustrate a pre-molding assembly of a header including an electrode, antenna, and attachment plate.

FIGS. 6C and 6D illustrate a first-shot molding assembly of the header, which may be the pre-molding assembly after a first molding step has been performed.

FIGS. 6E and 6F illustrate a second-shot molding assembly of the header, which may include the first-shot assembly after a second molding step has been performed.

DETAILED DESCRIPTION

Figure 1:
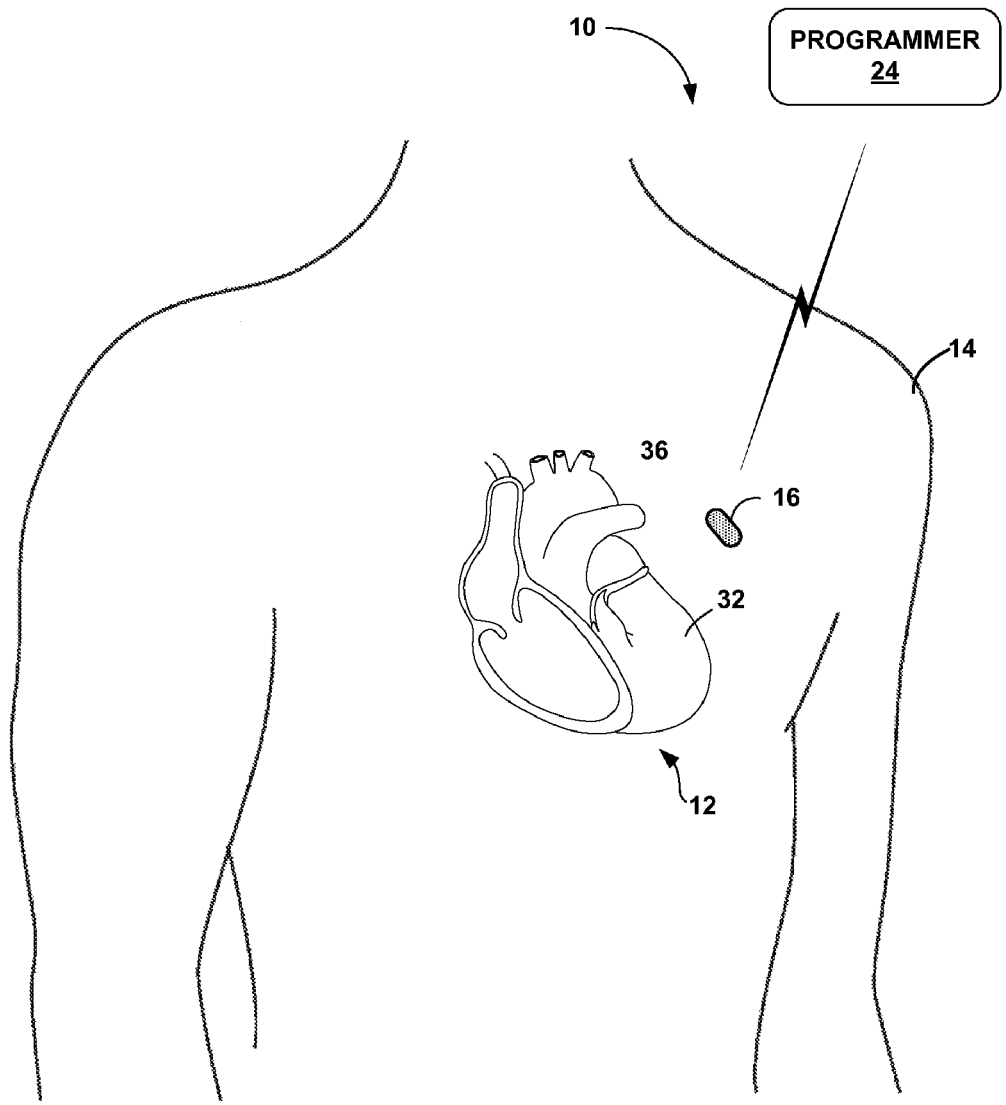
FIG. 1 is a conceptual diagram illustrating an example medical device system.

In some examples, components of implantable medical devices (IMDs) may be formed via molding processes, such as injection molding. In general, injection molding may produce parts from molding material, e.g., thermoplastic and thermosetting plastic materials. Such material may be forced or allowed to flow into a mold cavity, where the material may cool and harden to the configuration of the cavity, creating a molded part.

In the examples described herein, headers for IMDs may be formed via molding techniques. One or more components, e.g., an antenna, an electrode, and/or an attachment plate, may be positioned within the mold prior to introduction of the molding material such that the final molded part incorporates these components.

The examples described herein utilize two-shot molding processes. Two-shot molding processes use two molding steps to form a molded part, e.g., a molded header for an IMD. In some examples, the second molding step may be characterized as an overmold step, such that an assembly formed in the first molding step is overmolded in the second molding step.

In the examples described herein, one or more components of the IMD header, e.g., an antenna, electrode, and/or an attachment plate, may be positioned within a loading fixture and transferred to, e.g., loaded into, a first-shot mold. In some examples, the one or more components may be positioned freely within the first-shot mold, e.g., the components may not be required to be mechanically coupled to one another prior to positioning within the first-shot mold. In these examples, the first-shot mold may be specifically configured to accommodate the separate or free components.

In some examples, a first-shot mold configured to receive the free components may reduce the amount of steps required for forming the IMD, by eliminating a step in which the components are mechanically coupled to one another prior to molding. Similarly, positioning the individual components within the first-shot mold without having to mechanically couple, e.g., weld, them together beforehand may reduce the amount of handling of the components (which may, in some examples, be relatively small and delicate) by a user, which can prevent damage to the components.

After the one or more components are positioned within the first-shot mold, molding material may be injected into the first-shot mold to create a first-shot assembly that includes one or more features configured to interact with the second-shot mold or a molding material in the second molding step. For example, the first-shot assembly may include one or more protrusions extending from a surface of the first-shot assembly opposite the electrode and formed by at least one void defined within the first shot mold, where the one or more protrusions are configured to engage with a wall of the second-shot mold to substantially prevent coverage of the electrode with molding material during injection of a second shot molding material into the second-shot mold. In this way, the electrode surface may remain free of material in order to facilitate efficient and effective sensing and/or therapy delivery via the electrode.

As another example, the first-shot assembly may include one or more protrusions extending outward from a surface of the first shot assembly at a first portion or end of the first-shot assembly, where the one or more protrusions are configured to guide flow of a second-shot molding material that is introduced proximate to the first portion or end of the first shot assembly in the second-shot mold. More particularly, the protrusions are configured to guide flow of the second-shot molding material along a surface of the first-shot assembly, and toward a different, second portion or end of the first-shot assembly. The first portion or end of the first-shot assembly, when positioned within the second-shot mold, may be relatively proximate to the location where the second-shot molding material is introduced into the second-shot mold. The second portion or end may be less proximate to the location where the second shot molding material is introduced into the second shot mold than the first portion or end. The second portion or end may be opposite the first portion or end, in some examples. For example, the first portion or end may be a top portion or end of the first shot assembly, and the second portion or end may be a bottom portion or end of the first shot assembly. The first-shot assembly may be positioned into the second-shot mold, and the second molding step may subsequently be performed to overmold the first-shot assembly.

Forming a first-shot assembly that includes one or more protrusions configured to interact with the second-shot mold in the second molding step may provide one or more advantages. For example, a first-shot assembly that includes one or more protrusions extending from a surface of the first-shot assembly opposite the electrode may allow placement of the molding material during the second molding step to be more easily controlled, e.g., compared to a conventional overmolding process. In examples, placement of the molding material over the first-shot assembly may be confined to particular locations on the first-shot assembly. For example, the one or more protrusions may engage with a wall of the second-shot mold to press the electrode against an opposite wall and to substantially prevent coverage of the electrode with molding material during the second molding step. As another example, a first-shot assembly that includes one or more protrusions extending outward from one portion of the first-shot assembly and configured to guide flow of a second-shot molding material within the second-shot mold along a surface of the first-shot assembly toward another portion of the first-shot assembly may prevent defects, e.g., air bubbles, cracks, and the like, in the overmold during the second molding step by providing a more extended and continuous flow of the molding material over the first-shot assembly.

In some examples, as will be described in further detail below, the attachment plate of the header may be molded into the first-shot assembly and/or the second shot assembly. For example, at least a portion of the attachment plate may be covered by molding material such that the attachment plate is mechanically coupled to the header. The attachment plate may be configured to be mechanically coupled to a can of the IMD, e.g., via laser welding, such that the header is mechanically coupled to the can of the IMD.

FIG. 1 is a conceptual diagram illustrating an example system 10 that may be used to monitor one or more physiological parameters of patient 14. System 10 includes an implantable medical device (IMD) 16, which is coupled to programmer 24. IMD 16 may be a subcutaneous sensing device configured to sense signals indicative of one or more physiological parameters of patient 14. For example, IMD 16 may sense and/or store electrocardiogram (ECG) signals. In some examples, IMD 16 may be configured to sense ECG or other signals and detect arrhythmias, e.g., ventricular and/or supra-ventricular arrhythmias, based on the signals.

Although the examples described herein include IMD 16 configured to sense physiological signals of patient 14, in other examples IMD 16 may alternatively or additionally be configured to deliver therapy to patient 14. For example, IMD 16 may be an implantable leadless pacemaker that provides electrical signals to heart 12 via one or more electrodes (not shown in FIG. 1) on its outer housing. Additionally or alternatively, IMD 16 may sense electrical signals attendant to the depolarization and repolarization of heart 12 via electrodes on its outer housing. In some examples, IMD 16 provides therapy to patient 14 based on sensed physiological signals. Patient 14 is ordinarily, but not necessarily, a human patient.

In some examples, IMD 16 may be configured to be implanted proximate to heart 12, e.g., as illustrated in FIG. 1. In other examples, IMD 16 may be configured to be implanted proximate to or within another portion of the body of patient 14.

In the examples described herein, IMD 16 includes a header, which may include one or more components of IMD 16, and may be formed separately from the rest of IMD 16. In some examples, the header may include an antenna, at least one of the one or more electrodes, and/or an attachment plate configured to attach the header to another portion of IMD 16. The header may be formed via the molding techniques described herein.

In the example of FIG. 1, IMD 16 is positioned subcutaneously in a left pectoral region of patient 14. In other examples, however, IMD 16 may be positioned within any suitable region of patient 14. In some examples, depending on the location of implant, IMD 16 may include other sensing and/or stimulation functionalities. For example, IMD 16 may provide atrioventricular nodal stimulation, fat pad stimulation, vagal stimulation, or other types of neurostimulation, and/or may sense one or more parameters of heart 12 or another parameter of patient 12. In some examples, system 10 may include a plurality of leadless IMDs 16, e.g., to provide stimulation and/or sensing at a variety of locations.

FIG. 1 further depicts programmer 24 in communication with IMD 16. In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, other clinician, or patient, interacts with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD 16. For example, the user may use programmer 24 to retrieve information from IMD 16 regarding the rhythm of heart 12, trends therein over time, or arrhythmic episodes.

IMD 16 and programmer 24 may communicate via wireless communication using any techniques known in the art. Examples of communication techniques may include, for example, low frequency or radiofrequency (RF) telemetry, proximal inductive interaction, or tissue conductance communication, but other techniques are also contemplated. In some examples, programmer 24 may include a programming head that may be placed proximate to or in contact with the patient's body near the IMD 16 implant site in order to improve the quality or security of communication between IMD 16 and programmer 24.

Although the examples described herein refer to leadless IMD 16, IMD 16 may alternatively be coupled to one or more leads comprising one or more electrodes configured to sense the one or more physiological parameters of patient 14 and/or to deliver the therapy to heart 12 of patient 14. Additionally, although the examples herein describe monitoring physiological signals via IMD 16, IMD 16 may additionally or alternatively be configured for pacing therapy for heart 12, neuro stimulation therapy, defibrillation therapy, or cardioversion therapy via one or more electrodes of system 10.

Figure 2:
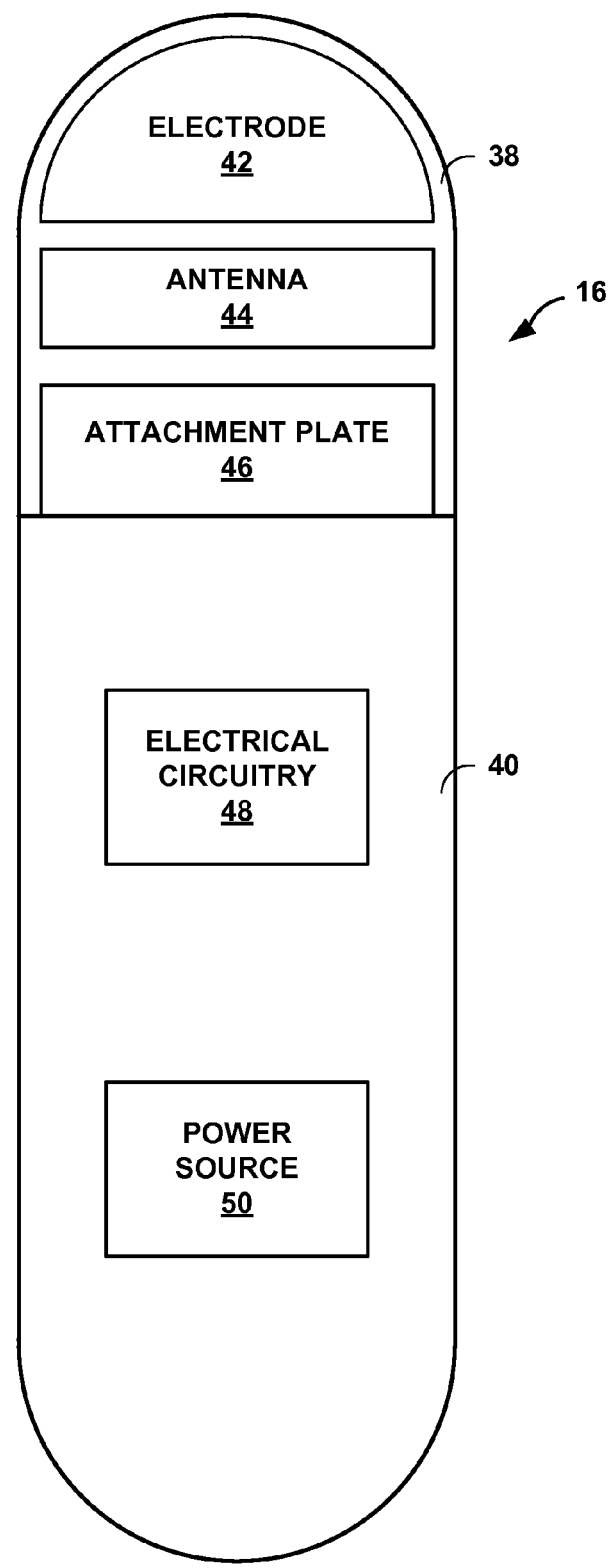
FIG. 2 is a conceptual diagram illustrating an example implantable medical device of the medical device system of FIG. 1.

FIG. 2 is a conceptual diagram further illustrating IMD 16. As shown in FIG. 2, IMD 16 may include header 38 coupled to body portion 40. In the examples described herein, header 38 may include electrode 42, antenna 44, and attachment plate 46. In particular, electrode 42, antenna 44, and attachment plate 46 may be molded into header 38 via a two-shot molding process, as described in further detail below. Body portion 40 of IMD 16 may include electrical circuitry 48 and power source 50, in some examples, which may be contained within a hermetic housing or can, e.g., formed of titanium or ceramic.

As shown in FIG. 2, header 38 includes at least one electrode 42. Electrode 42 may be configured to sense physiological signals of patient 14 and/or to deliver electrical stimulation therapy to patient 14, e.g., to treat a cardiac disorder of patient 14. IMD 16 may sense signals or deliver stimulation via electrode 42 in combination with another electrode, such as the housing of body portion 40. In some examples, electrode 42 may be coated with a material configured to improve performance, e.g., sensing or pacing performance. For example, electrode 42 may be coated with a conductive material such as Titanium Nitride (TiN).

Header 38 also includes antenna 44. Antenna 44 may be configured to transmit and/or receive electromagnetic signals for communication. For example, antenna 44 may be configured to transmit to and/or receive signals from programmer 24. Antenna 44 may be coupled to electrical circuitry 48 of IMD 16, which may drive antenna 44 to transmit signals to programmer 24, and may receive signals received from programmer 24 via antenna 44. In the example shown in FIG. 2, header 38 additionally includes attachment plate 46, which is configured to mechanically couple header 38 to body portion 40 of IMD 16, as will be described in further detail below.

In the example shown in FIG. 2, body portion 40 of IMD 16 is configured to house electrical circuitry 48 and power source 50. Electrical circuitry 48 may comprise one or more electrical circuits configured to perform any function of IMD 16. For example, the electrical circuitry 48 may be coupled to antenna 44 to receive and/or transmit signals. Electrical circuitry 48 may additionally or alternatively be configured to analyze physiological signals, e.g., signals sensed via electrode 42, and/or to control delivery of stimulation or other therapies. Body portion 40 is also configured to house power source 50, which may be configured to provide energy to various components of IMD 16, such as electrical circuitry 48.

Figure 3:
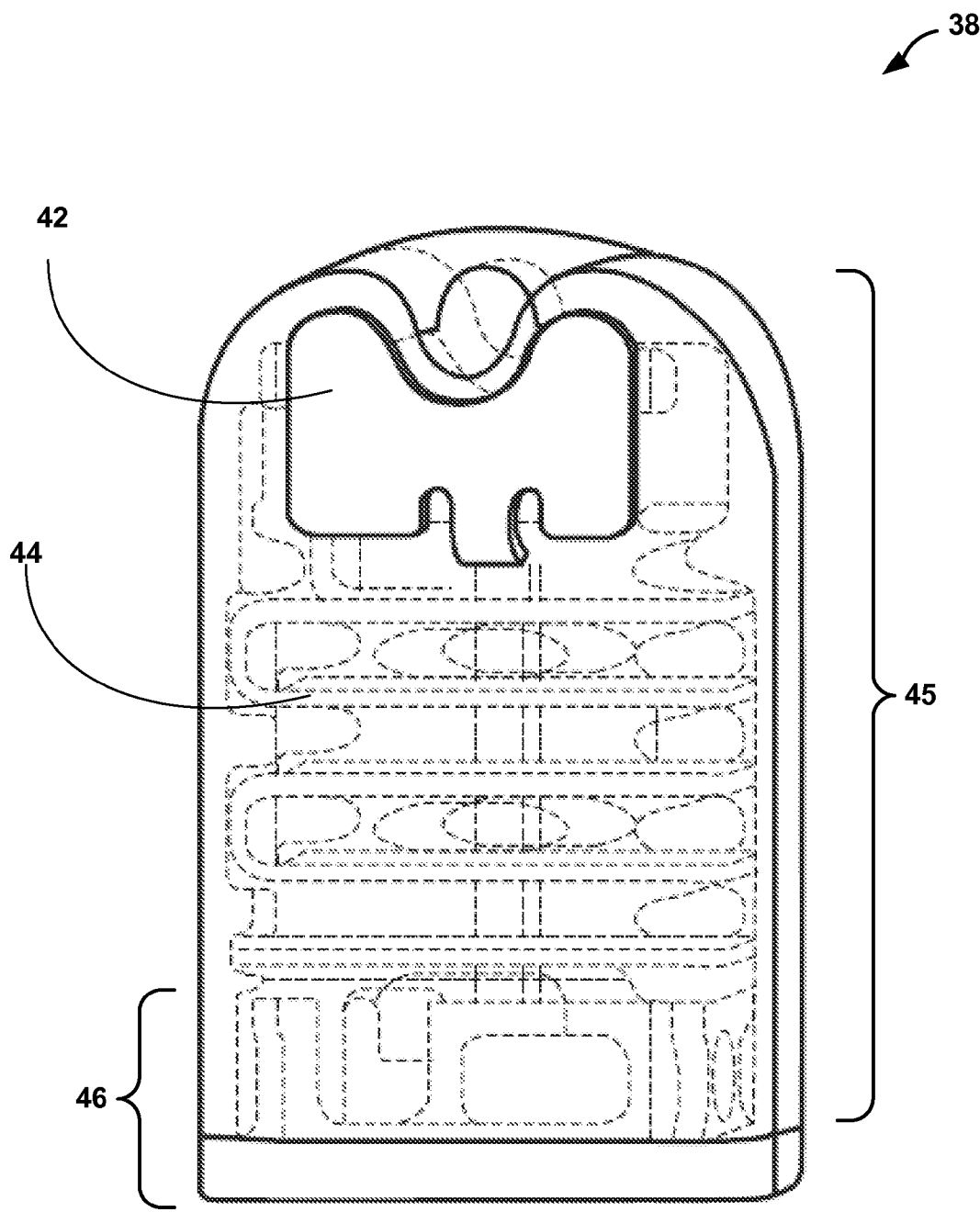
FIG. 3 is a schematic perspective diagram of an example header of an implantable medical device (IMD) formed via a two-shot molding process.

FIG. 3 is a schematic perspective diagram of header 38 after a two-shot molding process, and prior to mechanical and electrical coupling with body 40 of IMD 16. As shown in FIG. 3, electrode 42, antenna 44, and attachment plate 46 are at least partially molded into header 38. In some examples, at least a portion of attachment plate 46 and substantially entire electrode 42 may not be overmolded with molding material. Although electrode 42, antenna 44, and attachment plate 46 are visible in hidden lines in the schematic of FIG. 3, the components may not actually be visible from an outside view. For example, electrode 42, antenna 44, and attachment plate 46 may be at least partially overmolded such that the components are not entirely visible from an outside perspective, depending on the opacity of the molding material. The outer surface of header 38 may, in some examples, be relatively smooth and formed of hardened or cured molding material. However, for purposes of illustration, the components are shown in hidden (e.g., dashed) lines in FIG. 3.

Header 38 may, in some examples, be described herein as including a header body, which may be any components of header 38 besides attachment plate 46. For example, the header body of header 38 may include electrode 42, antenna 44, components of header 38 coupled to electrode 42 and/or antenna 44, molding material that holds the components of header 38 together, and the like. Thus, header 38 may include or comprise a header body and attachment plate 46. For example, as shown in FIG. 3, header 38 may include header body 45 and attachment plate 46.

Figure 4A:
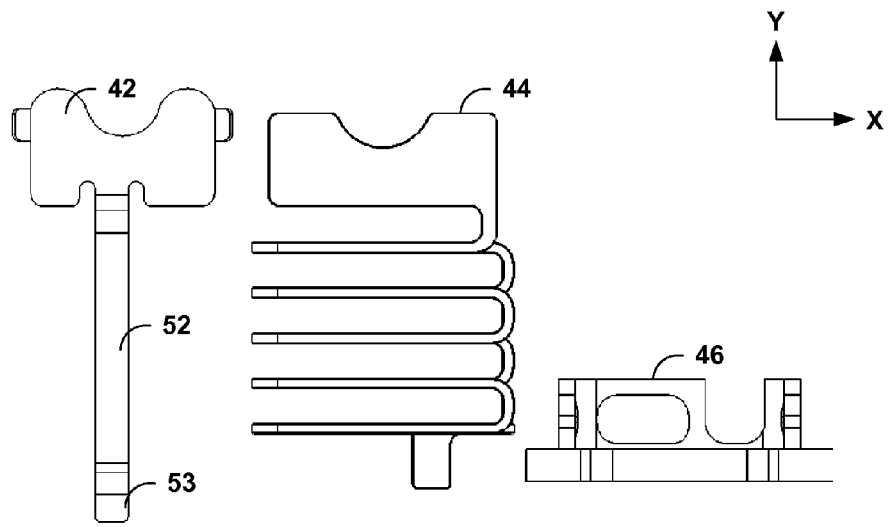
FIGS. 4A and 4B are schematic diagrams illustrating an example electrode, antenna, and attachment plate of a header of an IMD.
Figure 4B:
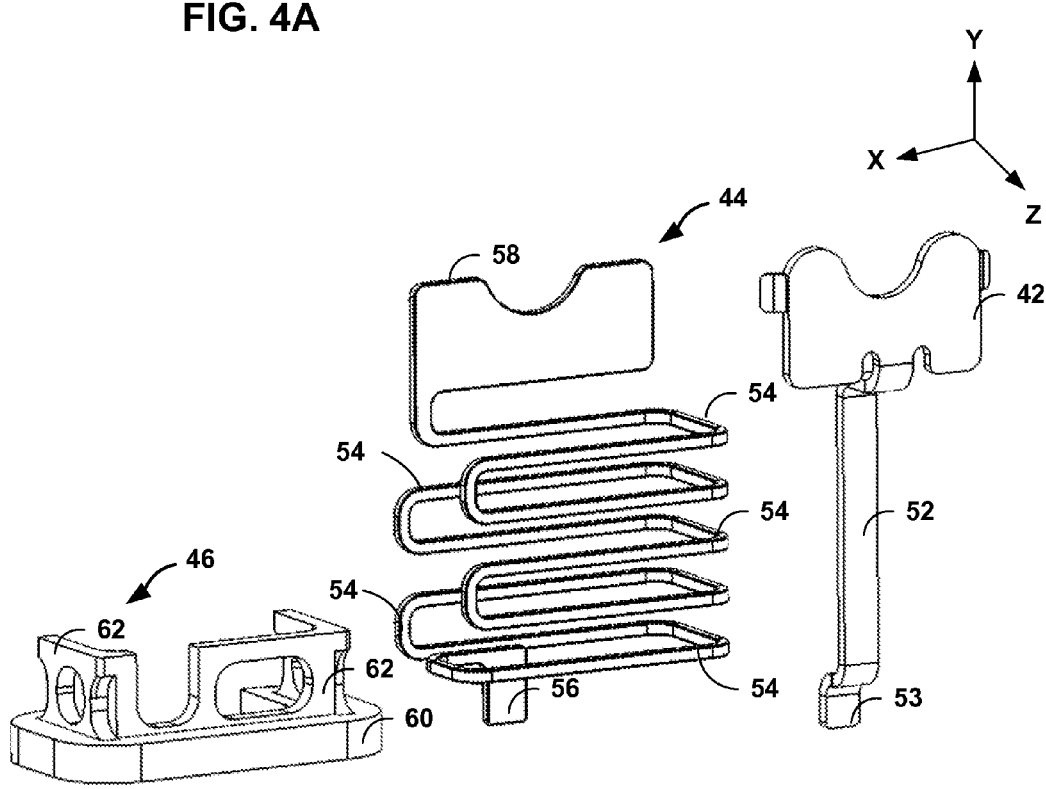

FIGS. 4A and 4B illustrate electrode 42, antenna 44, and attachment plate 46 prior to molding, e.g., in a free state. FIG. 4A is a two-dimensional schematic diagram illustrated in an x-y plane (orthogonal x-y axes are shown for purposes of illustration only), and FIG. 4B is a three-dimensional schematic diagram illustrated in an x-y-z plane (orthogonal x-y-z axes are shown for purposes of illustration only).

As shown, electrode 42 may be integral with (e.g., mechanically coupled to) shaft 52, which may be configured to stabilize electrode 42 during the molding process. For example, shaft 52 may be configured to interact with antenna 44, attachment plate 46, and/or one or more components of a molding fixture within which the assembly is placed during molding to stabilize electrode 42 during molding. In addition, shaft 52 may be configured to transmit to and receive electrical signals from electrode 42 during sensing and/or therapy delivery by IMD 16 after header 38 is incorporated into IMD 16. For example, shaft 52 may be electrically coupled to electrode 42, in addition to being mechanically coupled to electrode 42.

Electrode 42 may be formed from any suitable material configured for sensing physiological signals of patient 14 and/or for delivering electrical stimulation therapy to patient 14. For example, electrode 42 may be formed from titanium or a titanium alloy. In some examples, shaft 52 may be formed from the same material as electrode 42 while, in other examples, shaft 52 may be formed from a different material. Electrode 42 and shaft 52 may be formed from electrically conductive material(s) such that electrical signals may be transmitted and received via electrode 42 and shaft 52.

Electrode 42 may also have any dimensions suitable for incorporation into header 38. For example, electrode 42 may be approximately 0.170 inches wide (e.g., extending in an x-axis direction) and 0.109 inches long (e.g., extending in a y-axis direction). Similarly, shaft 52 may have any suitable dimensions. For example, shaft 52 may be approximately 0.030 inches wide (e.g., extending in an x-axis direction) and approximately 0.288 inches long (e.g., extending in a y-axis direction).

Antenna 44 may facilitate IMD 16 communications, e.g., communications with programmer 24 or other devices. Antenna 44 may be coupled to electrical circuitry 48, which may include a transmitter and/or receiver to transmit to and/or receive information from one or more other devices, such as other devices also implanted within patient 14, or other devices external to patient 14 (e.g., programmer 24). Antenna 44 may be configured to improve the ability of IMD 16 to receive and/or transmit signals, e.g., radio frequency (RF) signals.

In the examples described and illustrated herein, antenna 44 may be a three-dimensional antenna, which may be described as a meandering or serpentine antenna (e.g., in that it includes segments that meander in three-dimensions). For example, antenna 44 may be a three-dimensional antenna described in U.S. Patent Application Publication No. 2012/0001812 by Zhao et al., entitled "IMPLANTABLE MEDICAL DEVICE ANTENNA," published on Jan. 5, 2012, and incorporated herein by reference in its entirety. In other examples, antenna 44 may have another suitable configuration.

Antenna 44 may be described as an antenna that meanders in three dimensions. Antenna 44 may also be described as comprising a serpentine structure in three dimensions. As shown in FIG. 4B, three-dimensional antenna 44 includes a plurality of integral segments 54 running parallel and perpendicular to one another such that the segments 54 "meander" from top to bottom of antenna 44, e.g., in a substantially x- to y-direction. (For clarity of illustration, not all segments 54 are labeled in FIG. 4B). Antenna 44 may be considered to meander in three dimensions (or be considered a three-dimensional serpentine structure), because the individual segments 54 are arranged such that they "meander" between first, second, and third planes of antenna 44.

In one example, a spacing between parallel segments 54 of antenna 44 may be selected based on a ratio L/2n, where L is a maximum length of a volume of the antenna 44, and n is a number of meandering sections of antenna 44. In this example, the spacing between parallel segments 54 of antenna 44 may be constant. In other examples, spacing between segments 54 of antenna 44 may be determined in a different manner. In some examples, the spacing between parallel segments 54 of antenna 44 may not be selected to be constant.

As shown in FIG. 4B, antenna 44 may additionally include coupling structure 56 extending downward (e.g., in a substantially negative y-axis direction) from a bottommost segment 54. Coupling structure 56 may facilitate electrical connection of antenna 44 to one or more other components, such as electrical circuitry configured to communicate signals (e.g., electrical circuitry 48 of IMD 16 depicted in FIG. 2). In this manner, coupling structure 56 may be considered part of the antenna feed line. Another portion of the antenna feed line may be located within the housing of the IMD. Coupling structure 56 may, for example, be coupled to one or more other components (e.g., via one or more wires, traces, or other conductive structures) using various mechanisms known in the relevant art, including for example soldering, conductive adhesive, and the like. In other examples, coupling structure 56 may connect other portions of antenna 44 (e.g., segments other than the bottommost segment 54) to the other components of the IMD.

Antenna 44 may additionally include at least one antenna loading structure 58. Antenna loading structure 58 may be coupled to at least one of the plurality of segments 54. Antenna loading structure 58 is configured to provide conductive surface area available for telemetry. For example, the relatively large surface area of antenna loading structure may reduce the need for additional segments 54 of antenna 44 and, thus, maintain a relatively small size of header 38. The antenna loading structure 58 may also be configured to stabilize impedance of the antenna 44 and, thus, reduce the sensitivity of antenna 44 to electrical noise in the surrounding tissue environments. As another example, antenna loading structure 58 may be configured to provide a relatively large surface for fixation of molding material during the two-shot molding process, in comparison to, e.g., thin wires.

As shown in FIGS. 4A and 4B, header 38 also includes attachment plate 46, which includes base 60 and extensions 62 which extend outward from base 60 in a substantially y-axis direction. As will be described further below, base 60 is configured to be mechanically coupled to body 40 of IMD 16 to attach header 38 to body 40, and extensions 62 are configured to be at least partially covered in molding material during the molding process to mechanically couple attachment plate 46 within header 38. Header 38 may include a header body portion (e.g., including some or all components of header 38 other than attachment plate 46), in addition to attachment plate 46 configured to mechanically couple header 38 to body 40.

FIGS. 5A-5D illustrate various schematic diagrams of attachment plate 46. Attachment plate 46 is configured to be partially molded into header 38 and to subsequently be mechanically coupled to body 40 of IMD 16. In some examples, attachment plate 46 is configured to be mechanically coupled to body 40 via laser welding.

As mentioned above, attachment plate 46 includes base 60 and one or more extensions 62 extending from base 60. Extensions 62 are configured to be substantially molded into header 38 in the first and/or second molding steps of the two-shot molding processes described herein. In some examples, base 60 of attachment plate 46 remains substantially free of molding material in order to facilitate mechanical coupling of attachment plate 46 to body 40.

As shown in FIGS. 5A-5D, extensions 62 of attachment plate 46 may define one or more voids 63. Voids 63 may be configured to receive molding material in the first and/or second molding steps in order to create a strong bond of attachment plate 46 to the rest of header 38. For example, voids 63 provide space in which molding material can substantially surround portions of extensions 62 during molding. In this way, extensions 62 of attachment plate 46 may become substantially embedded within the molding material. Cured molding material positioned within voids 63 may withstand substantially more force in comparison to molding material positioned on a substantially constant surface that does not include voids 63. For example, molding material may become enmeshed within voids 63 making it harder to remove from attachment plate 46 when forces from various directions are applied.

Voids 63 may also function to receive components of a first or second-shot mold. For example, voids 63 may be configured to receive one or more mold cores, e.g., the one or more mold cores may extend through voids 63, to stabilize and support distal end 53 of shaft 52 and/or coupling structure 56 within the first shot mold. In this way, distal end 53 and coupling structure 56 may be prevented from being covered in molding material during the first molding step. For example, the one or more mold cores may push against distal end 53 and coupling structure 56 to substantially force distal end 53 and coupling structure 56 against a wall of a first or second shot mold such that molding material cannot cover distal end 53 and coupling structure 56 during molding. In this way, distal end 53 and coupling structure 56 may be kept free of molding material, or "flash free," during the first molding step. Distal end 53 and coupling structure 56 may subsequently be coupled to one or more feedthrough wires extending from body 40 into header 38 when header 38 is coupled to body 40. In other examples, voids 63 may be configured to receive other suitable types of mold cores, e.g., to stabilize other components of the assembly during molding.

As shown in FIGS. 5A-5D, base 60 of attachment plate 46 also defines space 65. Space 65 may be configured to receive, from body 40, the feedthrough wires configured to electrically couple components of body 40 of IMD 16 with components of header 38 of IMD 16 upon completion of header 38. For example, as shown in FIG. 20, lead extensions or feedthrough wires may extend upward through space 65 into header 38 to electrically couple electrical components, e.g., electrical circuitry 48 and power source 50, of body 40 with, e.g., distal end 53 and coupling structure 56.

Attachment plate 46 may be formed from any suitable material(s). For example, attachment plate 46 may include titanium or a titanium alloy.

FIGS. 6A and 6B illustrate pre-molding assembly 64, FIGS. 6C and 6D illustrate first-shot assembly 66, and FIGS. 6E and 6F illustrate second-shot assembly 68 of a first example header 38. As illustrated in FIGS. 6A and 6B, pre-molding assembly 64 includes electrode 42 (coupled to shaft 52), antenna 44, and attachment plate 46 prior to any molding steps. First-shot assembly 66, as shown in FIGS. 6C and 6D, includes electrode 42 (coupled to shaft 52), antenna 44, and attachment plate 46 after a first molding step of a two-shot molding process. As described herein, first-shot assembly 66 may include one or more features configured to interact with a second-shot mold during the second molding step of the two-shot molding process. Second-shot assembly 68, illustrated in FIGS. 6E and 6F, includes first-shot assembly 66 after the second molding step. The second molding step may, in some examples, be described as overmolding the first-shot assembly 66. The second-shot assembly 68 may be the finalized header 38 which may, after the second-shot molding step, be ready for coupling to body 40 of IMD 16 via attachment plate 46.

Figure 9:
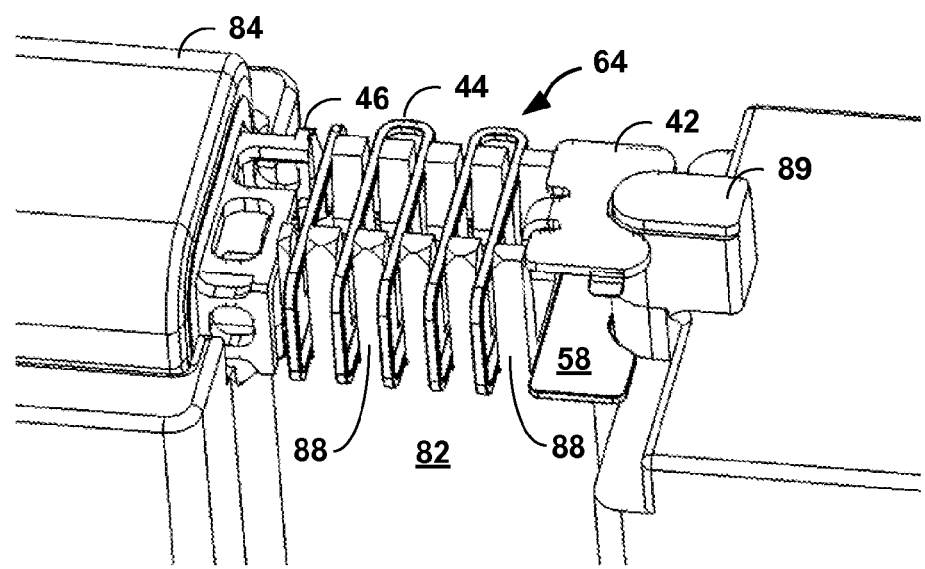
FIG. 9 is another schematic diagram illustrating a pre-molding assembly positioned within a loading fixture prior to transfer of the pre-molding assembly into a first-shot mold.

In some examples, pre-molding assembly 64 may be assembled prior to positioning within a loading fixture, e.g., loading fixture 82 (FIG. 9). For example, a user may arrange electrode 42 (including shaft 52), antenna 44, and attachment plate 46 in a particular configuration prior to positioning the assembly 64 within the loading fixture or other molding component, e.g., a first-shot mold.

In the example illustrated in FIGS. 6A and 6B, shaft 52 coupled to electrode 42 is positioned substantially through a middle opening of antenna 44 defined by segments 54 of antenna 44. A distal end 53 of shaft 52 (namely an end of shaft 52 positioned away from electrode 42) may be positioned such that the distal end 53 may be electrically coupled to one or more feedthrough wires or leads of body 40.

In the illustrated example, electrode 42 and antenna 44 are positioned such that electrode 42 and antenna loading structure 58 run substantially parallel to one another. In some examples, this configuration may provide a surface (e.g., a surface of antenna loading structure 58) on which one or more protrusions may be created opposite electrode 42 to prevent coverage of electrode 42 with molding material during the second molding step, as will be explained in further detail below.

As shown in FIGS. 6A and 6B, attachment plate 46 is positioned proximate to the distal end 53 of shaft 52 and a distal end of antenna 44 (e.g., coupling structure 56), both of which may be coupled to components within body 40 of IMD 16 when header 38 is coupled to body 40. Attachment plate 46 itself may be mechanically coupled to body 40 via any suitable technique, e.g., laser welding.

In the example illustrated in FIGS. 6A and 6B, electrode 42 and antenna loading structure 58 define grooves 67A and 67B, respectively, which may provide space for a suture hole in a finalized header 38. In some examples, the suture hole may be utilized to suture header 38 to tissue within patient 14 such that header 38 and IMD 16 do not migrate from a target implant site within patient 14. In other examples, IMD 16 may include another type of suitable fixation mechanism to prevent migration of IMD 16 within tissue of the patient 14.

FIGS. 6C and 6D illustrate first-shot assembly 66. First-shot assembly 66 may be formed by performing a first molding step over pre-molding assembly 64. As shown in FIGS. 6C and 6D, first-shot assembly 66 is formed to include one or more features configured to interact with a second shot mold or molding material during a second molding step subsequent to the first molding step. In particular, in the example assembly 66 illustrated in FIGS. 6C and 6D, assembly 66 includes protrusions 70A, 70B and protrusions 72A, 72B. In addition, first-shot assembly 66 includes suture-hole groove 69, created by grooves 67A, 67B of pre-molding assembly 64, which is configured to form a suture hole in the second-shot assembly 68, as shown in FIGS. 6E and 6F.

Protrusions 70A, 70B may be formed by first and second divots, respectively, defined within the first-shot mold. The first and second divots may be defined within the first-shot mold such that, when pre-molding assembly 64 is positioned within the first-shot mold, the first and second divots are positioned proximate to a surface of pre-molding assembly 64 opposite electrode 42 (e.g., proximate to antenna loading structure 58). In this way, when the first-shot molding material enters the first and second divots, protrusions 70A, 70B are formed by the first and second divots and extend from the surface of the first-shot assembly 66 opposite electrode 44. Protrusions 70A, 70B of first-shot assembly 66 may be configured to engage with a wall of the second-shot mold to substantially prevent coverage of electrode 42 during injection of the second-shot molding material into the second-shot mold. For example, protrusions 70A, 70B may engage with the wall of the second-shot mold to compress first-shot assembly 66 within the second shot mold such that the outer surface of electrode 42 is firmly pressed against a wall of the second-shot mold proximate the electrode 42.

Although FIGS. 6C and 6D illustrate two protrusions 70A, 70B, in other examples, first-shot assembly 66 may include more or less than two protrusions extending from a surface of the first-shot assembly 66 opposite electrode 42. In these examples, the first-shot mold may include any suitable number of divots configured to receive the first-shot molding material and form the one or more protrusions 70 extending from the surface of the first-shot assembly 66.

As shown in FIGS. 6C and 6D, first-shot assembly 66 also includes protrusions 72A and 72B extending outward from a surface at a first portion or end of the first-shot assembly. In this way, protrusions 72A, 72B may be configured to guide flow of a second shot molding material that is introduced proximate to the first portion or end of the first-shot assembly 66 in the second-shot mold. For example, molding material may be introduced into a mold cavity of the second-shot mold proximate to the end of first-shot assembly 66 that includes protrusions 72A, 72B. Protrusions 72A, 72B may be configured to guide flow of the second-shot molding material toward a different, second portion or end of first-shot assembly 66.

In some examples, first-shot assembly 66 may define a longitudinal axis that extends between the first and second ends of the first-shot assembly 66. The first end of first-shot assembly 66, on which protrusions 72A, 72B are formed, may be a portion of first-shot assembly 66 proximate to electrode 42 and/or antenna loading structure 58, in some examples. The first end or portion of first-shot assembly 66 may, in some examples, be referred to as a substantially top portion of first-shot assembly 66. The second end or portion of first-shot assembly 66, toward which protrusions 72A, 72B may guide molding material in the second shot mold, may be a portion or end of first-shot assembly 66 proximate to attachment plate 46 and/or distal end 53 of shaft 52 and/or antenna coupling structure 56, in some examples. The second end or portion of first-shot assembly 66 may, in some examples, be referred to as a substantially bottom portion of first-shot assembly 66.

In the example illustrated in FIGS. 6C and 6D, the protrusions 72A, 72B are positioned proximate to electrode 42 and antenna loading structure 58 and extend between electrode 42 and antenna loading structure 58, e.g., in a substantially transverse direction relative to the longitudinal axis 73 of the header in FIGS. 6C, 6D. Protrusions 72A, 72B may be configured to direct or guide flow of molding material along a surface of the first-shot assembly from a first portion or end of the first-shot assembly 66 toward a second portion or end of the first-shot assembly 66 within the second-shot mold during the second molding step.

In some examples, protrusions 72A, 72B may be defined by a particular shape, contour, texture, or other characteristic that is configured to direct or guide flow of the molding material during the second molding step in a particular manner. For example, protrusions 72A, 72B may be relatively smooth such that molding material may flow around the protrusions from the first portion of the first-shot assembly 66 to the second portion of the first-shot assembly 66. The protrusions 72A, 72B may, in some examples, be rounded to facilitate flow of the molding material through the second shot mold.

Figure 13:
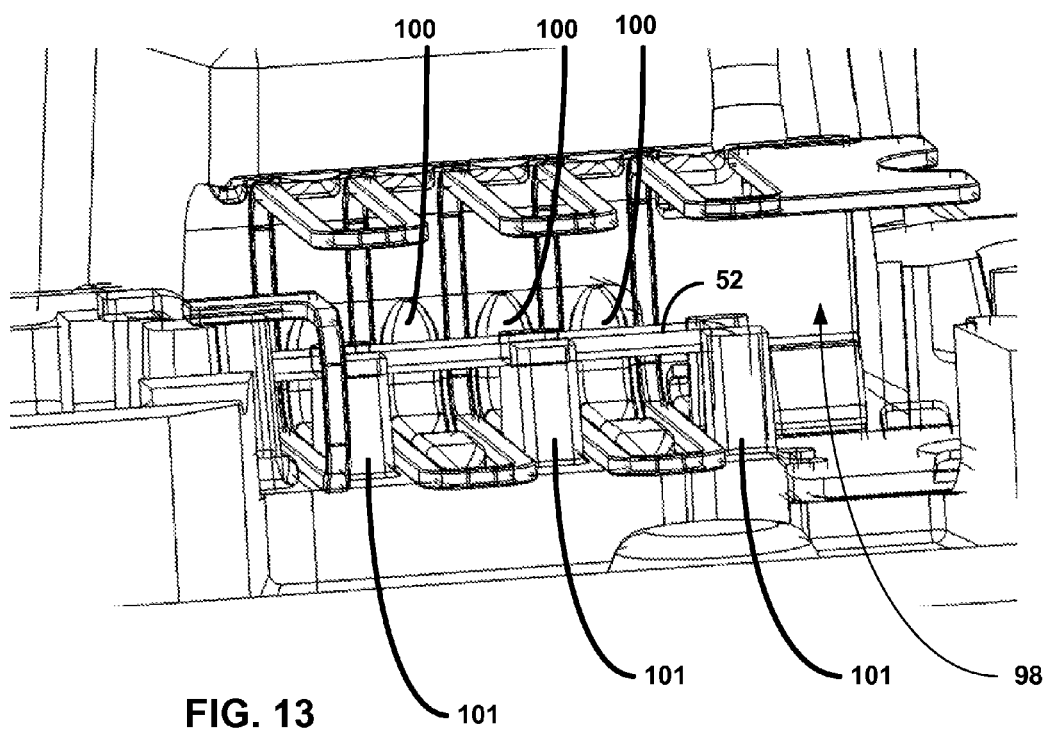
FIG. 13 is a schematic diagram illustrating a cross-section of a mold cavity of the first-shot mold when the pre-molding assembly is positioned within the mold cavity.

In some examples, features of the first-shot mold may create one or more open regions 71 in the first-shot assembly 66, e.g., regions that did not fill with molding material in the first molding step. For example, as illustrated in FIG. 13, alignment features 100 and support features 101 extend into pre-molding assembly 64 within the first-shot mold, such that molding material may not enter the spaces occupied by features 100 and 101 in the first molding step. The spaces occupied by features 100 and 101 in the first molding step may, thus, define open regions 71 in the first-shot assembly 66.

Protrusions 72A, 72B may be configured to direct molding material in the second molding step through open regions 71 by guiding the molding material in a particular manner. In some examples, protrusions 72A, 72B contact walls of the second shot mold to keep first-shot assembly 66 central during the second molding step and to block flow of the molding material from moving in a particular direction during the second molding step, e.g., to prevent entrapment of air within the molding material.

As an example, protrusions 72A, 72B may be configured to engage with walls of the second shot mold to stabilize first-shot assembly 66 in a central position within the second shot mold. Protrusions 72A, 72B may engage with the walls of the second shot mold such that molding material is initially prevented from moving along the sides of first-shot assembly 66 and directly into regions 71, and instead is substantially forced along the plane of pre-molding assembly 66 that is proximate to antenna loading structure 58 and protrusions 70A, 70B. The molding material may subsequently enter regions 71 after moving along the plane of pre-molding assembly 66 that is proximate to antenna loading structure 58. Guidance of molding material by protrusions 72A, 72B during the second molding step will be described in further detail with respect to FIG. 19.

As with protrusions 70A and 70B, protrusions 72A and 72B may be formed by two divots defined within the first-shot mold. In the example illustrated in FIGS. 6A-6D, the divots may be defined within the first-shot mold such that, when pre-molding assembly 64 is positioned within the first-shot mold, the two divots are positioned proximate to and extending between electrode 42 and antenna loading structure 58 on the sides of pre-molding assembly 64. In this way, when the first-shot molding material enters the divots, protrusions 72A, 72B are formed on a substantially top portion of first-shot assembly 66, e.g., proximate to and extending between electrode 42 and antenna loading structure 58. As discussed above, protrusions 72A, 72B may be configured to guide molding material from a substantially top portion toward a substantially bottom portion of the first-shot assembly 66 within the second-shot mold, e.g., to provide substantially even coverage of first-shot assembly 66 with molding material and/or to prevent defects within the cured second shot molding material.

Although FIGS. 6C and 6D illustrate two protrusions 72A, 72B, in other examples, first-shot assembly 66 may include more or less than two protrusions extending from a substantially top portion of the first-shot assembly. In these examples, the first-shot mold may include any suitable number of divots configured to receive the first-shot molding material and form the one or more protrusions 72.

FIGS. 6E and 6F illustrate second-shot assembly 68, which may also be referred to as header 38. That is, second-shot assembly 68 may be the finalized header 38. Second-shot assembly 68 is formed by performing a second molding step over first-shot assembly 66, e.g., an overmolding step, within a second-shot mold. In the examples illustrated in FIGS. 6E and 6F, second-shot assembly 68 may define suture hole 74, which may be formed within the space defined by suture-hole groove 69 during the second molding step.

As illustrated in FIGS. 6E and 6F, the second molding step may leave one or more components of second-shot assembly 68 exposed. For example, in the example illustrated in FIGS. 6E and 6F, electrode 42, distal end 53 of shaft 52 (which may be integral with electrode 42), and base 60 of attachment plate 46 may not be overmolded in the second molding step. Electrode 42 may be kept free of molding material (e.g., "flash" free) such that electrode 42 may clearly sense physiological signals and/or deliver stimulation therapy when IMD 16 is implanted within a patient. Distal end 53 of shaft 52 may be kept free of molding material such that distal end 53 of shaft 52 may be electrically coupled to one or more feedthrough wires or leads from body 40 to electrically couple electrode 42 to electrical components of body 40. Similarly, although not shown in FIGS. 6E and 6F, antenna coupling structure 56 may also be kept free of molding material in order to facilitate electrical coupling with wires or leads from body 40 to electrically couple antenna 44 to electrical components of body 40. Base 60 of attachment plate may be kept free of molding material in order to facilitate mechanical coupling of attachment plate 46 (and, consequently, header 38) to body 40 of IMD 16.

Figure 7:
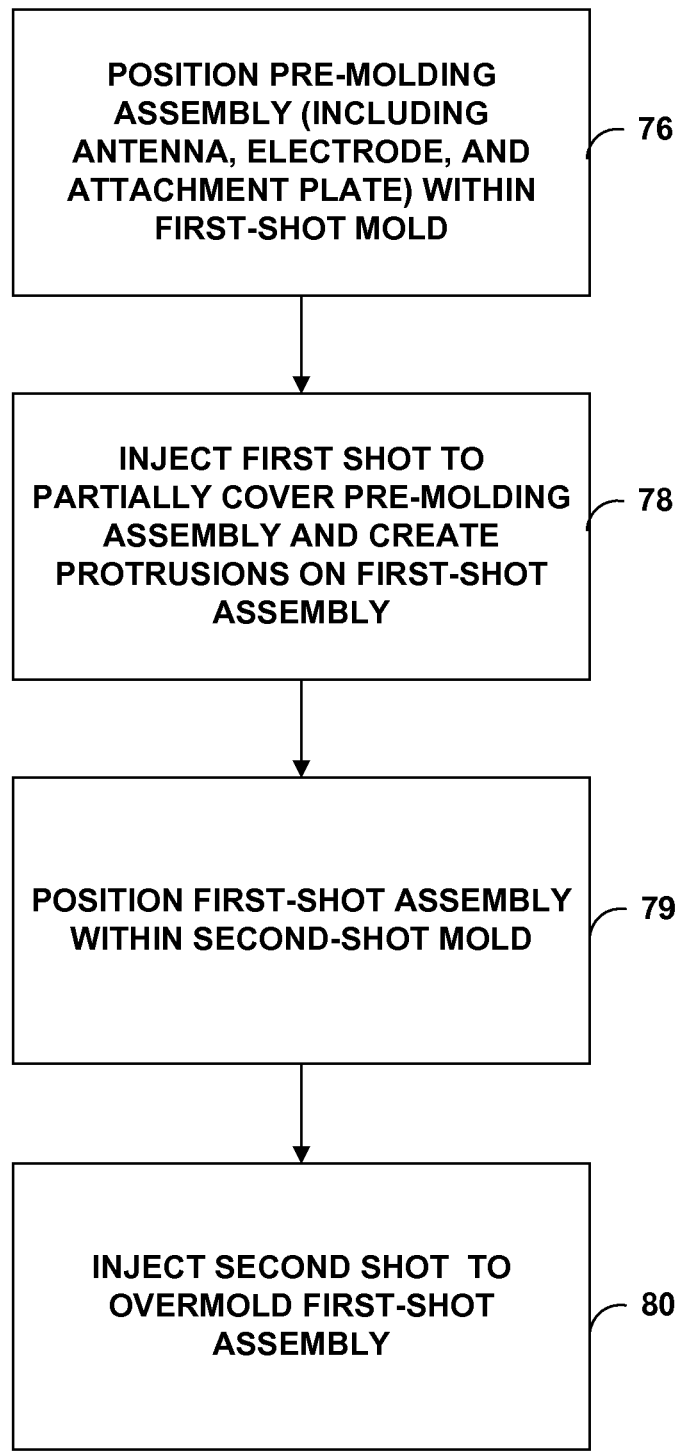
FIG. 7 is a flow diagram illustrating an example technique for forming a header for an IMD via a two-shot molding process.

FIG. 7 is a flow diagram illustrating an example technique for forming header 38 via a two-shot molding process.

According to the technique illustrated in FIG. 7, pre-molding assembly 64 (e.g., electrode 42 and shaft 52, in examples in which electrode 42 is integral with shaft 52, antenna 44, and attachment plate 46) is positioned within a first-shot mold (76). In some examples, pre-molding assembly 64 may be positioned within the first-shot mold via a loading fixture, as will be described in greater detail with respect to FIGS. 8-11. In some examples, the loading fixture may comprise one or more components configured to align and/or constrain the electrode 42, antenna 44, and attachment plate 46 in a particular configuration relative to one another. The loading fixture may interface with a molding cavity of the first-shot mold, and the pre-molding assembly 64 may be aligned within a cavity of the first-shot mold and transferred from the loading fixture to the first-shot mold. The loading fixture may be removed after the pre-molding assembly 64 is positioned within the first-shot mold and before a first-shot molding material is injected into the first-shot mold.

According to the technique illustrated in FIG. 7, after positioning of the pre-molding assembly 64 within the first-shot mold, a first shot molding material is injected into the first-shot mold to at least partially cover the pre-molding assembly 64 and to create one or more protrusions on the first-shot assembly 66 (78). For example, as described above, the first-shot mold may include one or more divots configured to receive molding material during the first molding step such that, when the molding material has hardened, first-shot assembly 66 includes one or more protrusions (e.g., protrusions 70A, 70B, 72A, 72B) configured to interact with a second-shot mold and/or second-shot molding material.

The first-shot molding material may be any suitable molding material. For example, the first-shot molding material may be a thermoplastic material, such as medical grade polyurethane. In some examples, the material may have a durometer of between approximately 50 and 90 on a shore D scale. The molding material may, in some examples, be heated to approximately 450 degrees Fahrenheit and injected into a molding cavity which is relatively cooler, e.g., approximately 85 degrees Fahrenheit. The molding material may harden on contact with the relatively cooler molding cavity, thus hardening before being ejected out of the cavity.

According to the technique shown in FIG. 7, upon creating the first-shot assembly 66 including the protrusions (e.g., protrusions 70A, 70B and/or protrusions 72A, 72B), the first-shot assembly 66 may be positioned within a second-shot mold (79). In some examples, a loading fixture may be used to position the first-shot assembly 66 within the second-shot mold, while, in other examples, a loading fixture may not be used. After the first-shot assembly 66 is positioned within the second-shot mold, a second-shot molding material is injected into a second-shot mold to at least partially overmold the first-shot assembly 66 (80). As described with respect to FIGS. 6E and 6F, various components of the second-shot assembly 68 may not be overmolded during the molding process. That is, they may be kept free of molding material. For example, electrode 42 may not be covered by molding material during the second molding step, e.g., may be kept "flash free". In this way, electrode 42 may be able to sense and/or deliver therapy via electrode 42 after the header 38 is formed. After hardening or curing of the second-shot molding material, header 38 may be substantially complete and ready for mechanical coupling to body 40 of IMD 16.

The second-shot mold may include various features configured to interact with the interaction features created on the first-shot mold. For example, in examples in which the interaction features are protrusions 70A, 70B configured to engage with a surface of the second-shot mold to prevent coverage of electrode 42 with molding material, the second-shot mold may include a surface proximate to a surface of the first-shot assembly that is opposite the electrode 42 (e.g., a surface proximate to antenna loading structure 58) such that the protrusions 70A, 70B may engage with the surface of the second-shot mold.

In some examples, the second-shot mold may be a different mold than the first-shot mold. In these examples, prior to injection of the second-shot molding material into the second-shot mold, the first-shot assembly may be moved and positioned within the second-shot mold. In some examples, a second loading fixture may be utilized to transfer the first-shot assembly 66 to the second-shot mold.

The second-shot molding material may be any suitable molding material. For example, the second-shot molding material may be a thermoplastic material, such as a medical grade polyurethane. In some examples, the material may have a durometer of between approximately 50 and 90 on a shore D scale. The molding material may, in some examples, be heated to approximately 450 degrees Fahrenheit and injected into a molding cavity which is relatively cooler, e.g., approximately 85 degrees Fahrenheit. The molding material may harden on contact with the relatively cooler molding cavity, thus hardening before being ejected out of the cavity.

Figure 8:
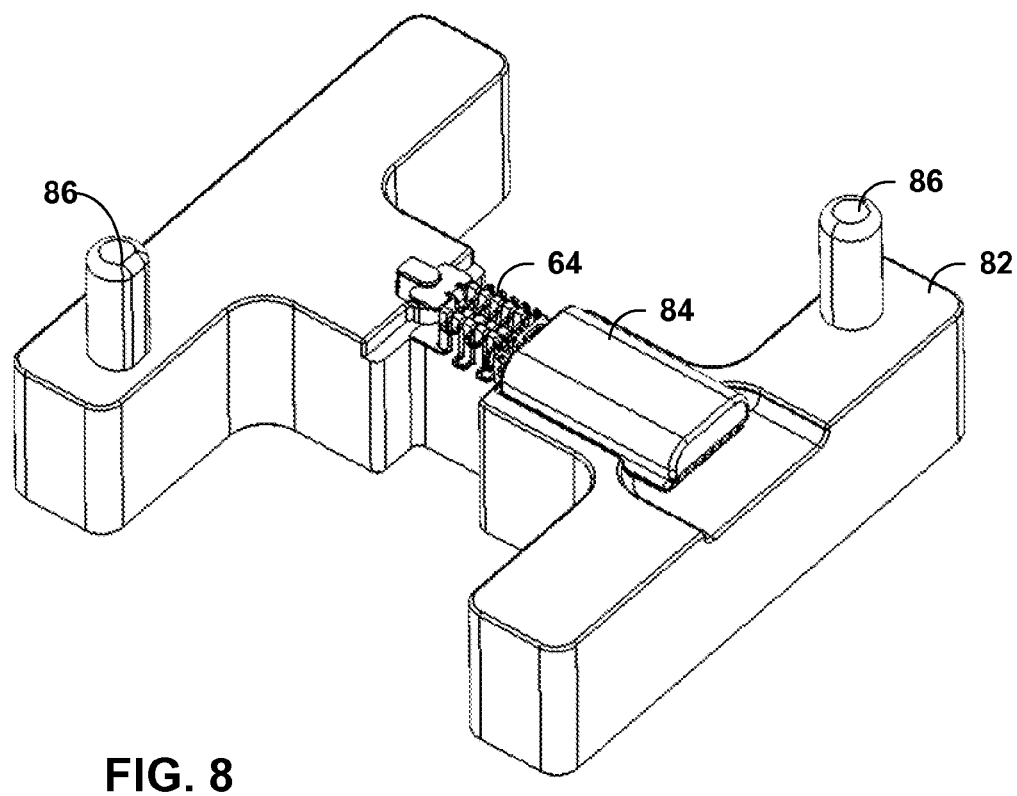
FIG. 8 is a schematic diagram illustrating a pre-molding assembly positioned within a loading fixture prior to transfer of the pre-molding assembly into a first-shot mold.
Figure 10:
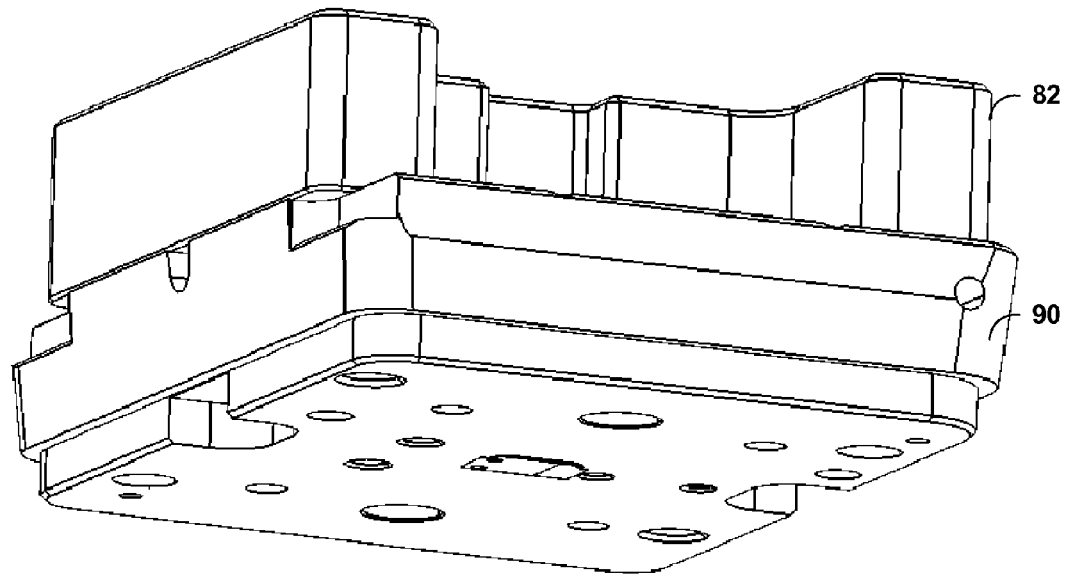
FIG. 10 is a schematic diagram illustrating an example first-shot mold and loading fixture during transfer of a pre-molding assembly from the loading fixture to the first-shot mold.

FIG. 8 is a schematic diagram illustrating pre-molding assembly 64 (FIGS. 6A, 6B) positioned within loading fixture 82 prior to the first molding step of the two-shot molding process. Loading fixture 82 is configured to align pre-molding assembly 64 (e.g., to align the individual components of pre-molding assembly 64) such that pre-molding assembly 64 may be transferred to first-shot mold 90 in an appropriate configuration (FIG. 10).

As shown in FIG. 8, the components of pre-molding assembly 64 may be positioned and secured/stabilized on loading fixture 82. Loading fixture 82 may include predefined alignment features configured to receive the components of pre-molding assembly 64 and maintain alignment of the components during transfer to the first-shot mold 90. In some examples, loading fixture 82 may be formed such that the components of assembly 64 are held in place within loading fixture 82 by gravity, prior to transfer of the components to first-shot mold 90. For example, loading fixture 82 may include one or more grooves or alignment features within which the components of assembly 64 may be positioned or loaded, as shown in more detail in FIG. 9.

Loading fixture 82 is configured to interface with first-shot mold 90 to transfer pre-molding assembly 64 to first-shot mold 90. For example, loading fixture 82 may include pins 86 extending from a surface of loading fixture 82 and configured to engage with first-shot mold 90 to substantially secure first-shot mold 90 and loading fixture 82 to one another during transfer of assembly 64 to first-shot mold 90. The pins 86 may align with corresponding holes in the first-shot mold 90 to secure the mold 90 and loading fixture to one another. Although FIG. 8 illustrates pins 86 configured to engage with first-shot mold 90, in other examples first-shot mold 90 may include any mechanism suitable for aligning and/or mechanically coupling loading fixture 82 with first-shot mold 90.

In the example shown in FIG. 8, mold pickout 84 may be positioned over a portion of pre-molding assembly 64. Mold pickout 84 may be configured to substantially cover particular portions of pre-molding assembly 64 during the first molding step to prevent molding material from contacting the covered portions of assembly 64. For example, mold pickout 84 may be configured to cover base 60 of attachment plate 46, antenna coupling structure 56 of antenna 44, and distal end 53 of shaft 52 during the first molding step. In this way, base 60, antenna coupling structure 56, and distal end 53 may remain free of molding material during the first molding step. Mold pickout 84 may be aligned in loading fixture 82 and subsequently transferred to first-shot mold 90 along with pre-molding assembly 64.

FIG. 9 is a schematic diagram illustrating assembly 64 positioned within loading fixture 82. Loading fixture 82 may comprise any components suitable for aligning electrode 42, shaft 52, antenna 44, and attachment plate 46 substantially freely within loading fixture 82. For example, loading fixture 82 may facilitate positioning of the components of assembly 64 within loading fixture 82 without requiring mechanical coupling of the components to one another prior to loading into loading fixture 82.

In the example shown in FIG. 9, loading fixture 82 includes alignment features 88 which define cavities within which antenna 44 or, more particularly, segments 54 of antenna 44, may be positioned. For example, depending upon the dimensions and configuration of antenna 44, loading fixture 82 may be formed to include cavities which line up with and are thus configured to receive various portions and/or segments of antenna 44, as shown in FIG. 9.

In some examples, loading fixture 82 also includes stabilizing structure 89 configured to stabilize electrode 42 and antenna loading structure 58 of antenna 44 within loading fixture 82. As shown in FIG. 9, stabilizing structure 89 is configured to engage grooves 67A, 67B of pre-molding assembly 64 to substantially prevent motion (e.g., side-to-side motion) of electrode 42 and antenna loading structure 58. In particular, in the example of FIG. 9, stabilizing structure 89 is positioned within grooves 67A, 67B to stabilize pre-molding assembly 64 within loading fixture 82.

FIG. 10 is a schematic diagram illustrating an example first-shot mold 90 and loading fixture 82 during transfer of assembly 64 to first-shot mold 90. As illustrated in FIG. 10, loading fixture 82 is configured to engage with first-shot mold 90 during transfer of pre-molding assembly 64 to first-shot mold 90. For example, loading fixture 82 may include pins 86 (FIG. 8) which are configured to be positioned within one or more cavities (not shown) defined within first-shot mold 90 to substantially align loading fixture 82 with first-shot mold 90 in the manner illustrated in FIG. 10. Pins 86 and the cavities defined within first-shot mold 90 may be positioned such that, when pins 86 are inserted into the cavities, the pre-molding assembly 64 is aligned with a molding cavity of the first-shot mold 90. The pre-molding assembly 64 may subsequently be transferred into the molding cavity of the first-shot mold 90.

Figure 11:
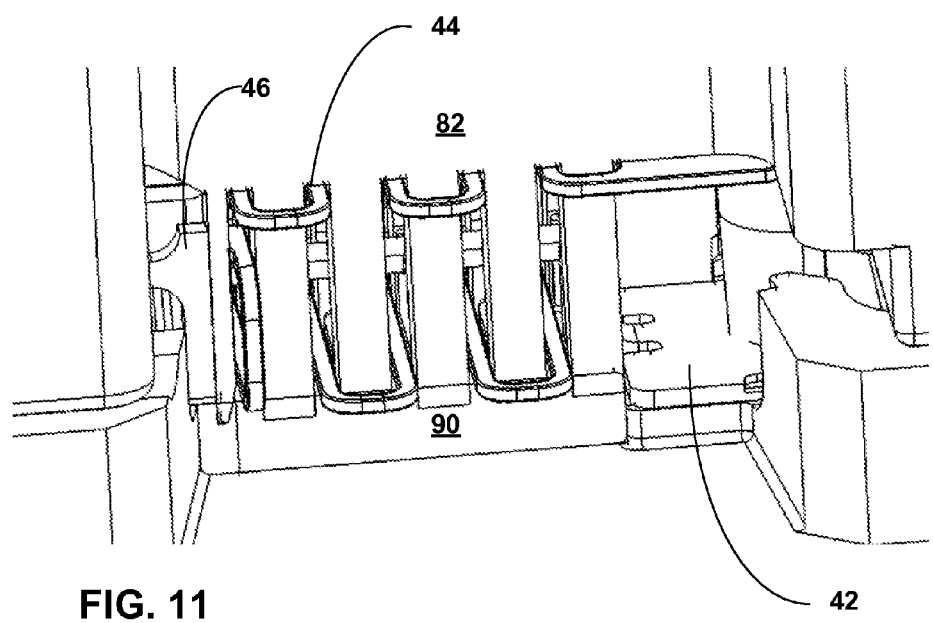
FIG. 11 is a schematic diagram illustrating a cross-section of the first-shot mold and loading fixture of FIG. 10.

FIG. 11 is a schematic diagram illustrating a cross-section of the assembly shown in FIG. 10. In particular, FIG. 11 illustrates assembly 64 (including electrode 42, antenna 44, and attachment plate 46) positioned within loading fixture 82 when loading fixture 82 is engaged with first-shot mold 90 prior to full transfer of assembly 64 to first-shot mold 90. Loading fixture 82 is configured to interface with first-shot mold 90 to guide assembly 64 into a constrained position within first-shot mold 90.

Loading fixture 82 and first-shot mold 90 may interface in any manner suitable to transfer pre-molding assembly 64 from loading fixture 82 to first-shot mold 90.

Figure 12:
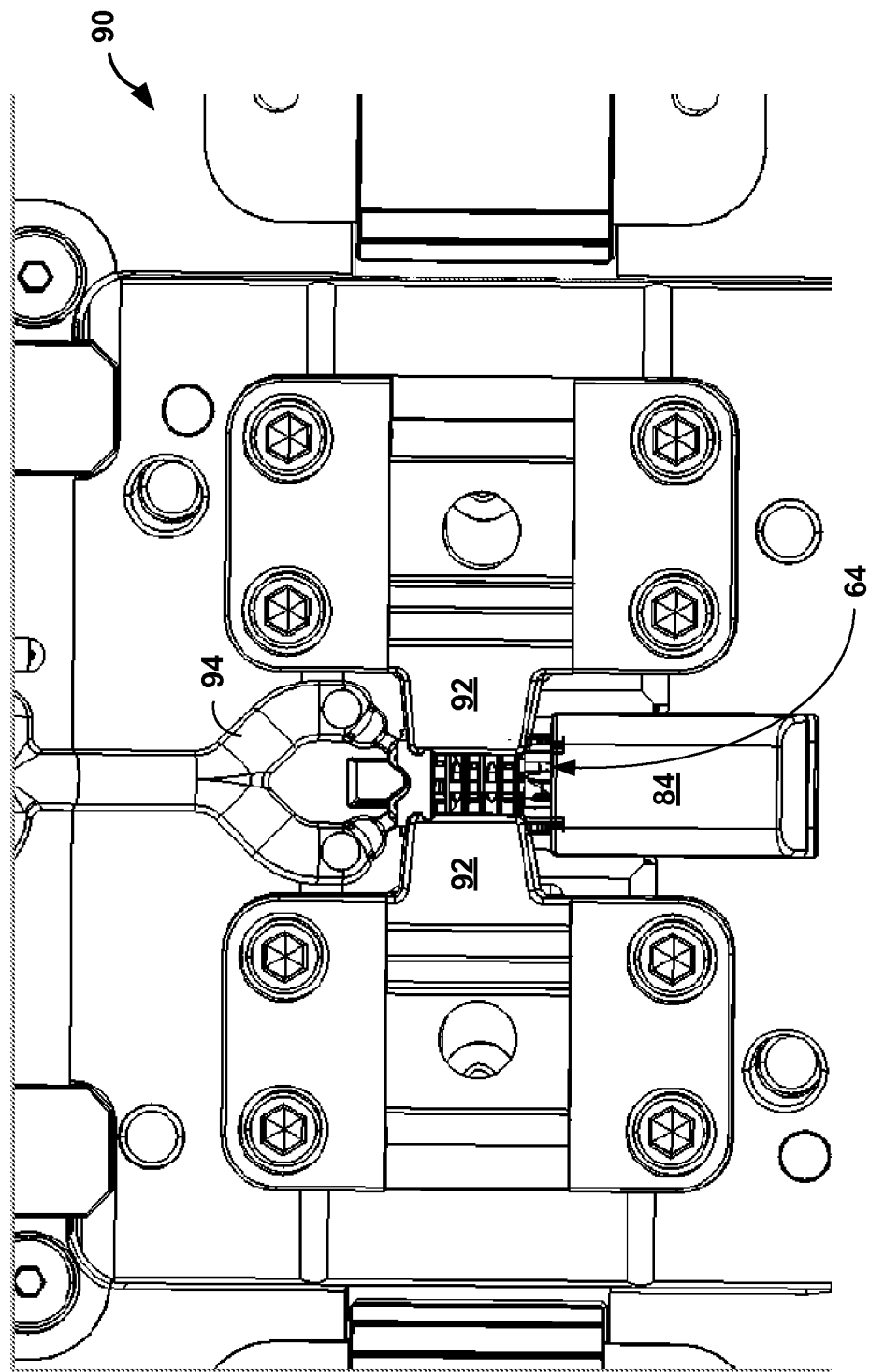
FIG. 12 is a schematic diagram illustrating the pre-molding assembly positioned in the first-shot mold after the loading fixture has been removed.

FIG. 12 illustrates pre-molding assembly 64 positioned in first-shot mold 90 after loading fixture 82 has been removed. In the example illustrated in FIG. 12, first-shot mold 90 includes cams 92 configured to hold or maintain pre-molding assembly 64 in place while loading fixture 82 is removed, e.g., when pre-molding assembly 64 is transferred from loading fixture 82 to first-shot mold 90. In particular, cams 92 may engage with pre-molding assembly 64 (e.g., via one or more alignment features, not shown in FIG. 12) while pre-molding assembly 64 is positioned within loading fixture 82 and may hold pre-molding assembly 64 within first-shot mold 90 while loading fixture 82 is removed.

As shown in FIG. 12, mold pickout 84 may also be transferred from loading fixture 82 to first-shot mold 90, in some examples. In this way, mold pickout 84 may keep one or more components of pre-molding assembly 64 free and clear of molding material during the first molding step of the two-shot molding process.

First-shot mold 90 also includes molding material distributor 94, which may be configured to deliver first-shot molding material into the mold cavity 98 (FIG. 13) of first-shot mold 90. Distributor 94 may be connected to the mold cavity 98 via connectors 96 (shown in FIG. 14), through which distributor 94 may deliver the first-shot molding material into the mold cavity 98.

FIG. 13 is a schematic diagram illustrating a cross-section of mold cavity 98 of first-shot mold 90 when pre-molding assembly 64 is positioned within mold cavity 98. As illustrated in FIG. 13, first-shot mold 90 may include alignment features 100 configured to stabilize and align pre-molding assembly 64 within mold cavity 98. In particular, alignment features 100 may be configured to extend between segments of antenna 44 to stabilize antenna 44 within mold cavity 98. In some examples, stabilization of antenna 44 via alignment feature 100 may result in stabilization of other components of pre-molding assembly 64 within cavity 98 because the components of pre-molding assembly 64 may support one another. In some examples, the alignment features 100 may be integral with cams 92. In the example illustrated in FIG. 13, first-shot mold 90 also includes support features 101 configured to support shaft 52 within cavity 98. In some examples, alignment features 100 and/or support features 101 may create open regions 71 (FIGS. 6C, 6D) within first-shot assembly 66.

Figure 14:
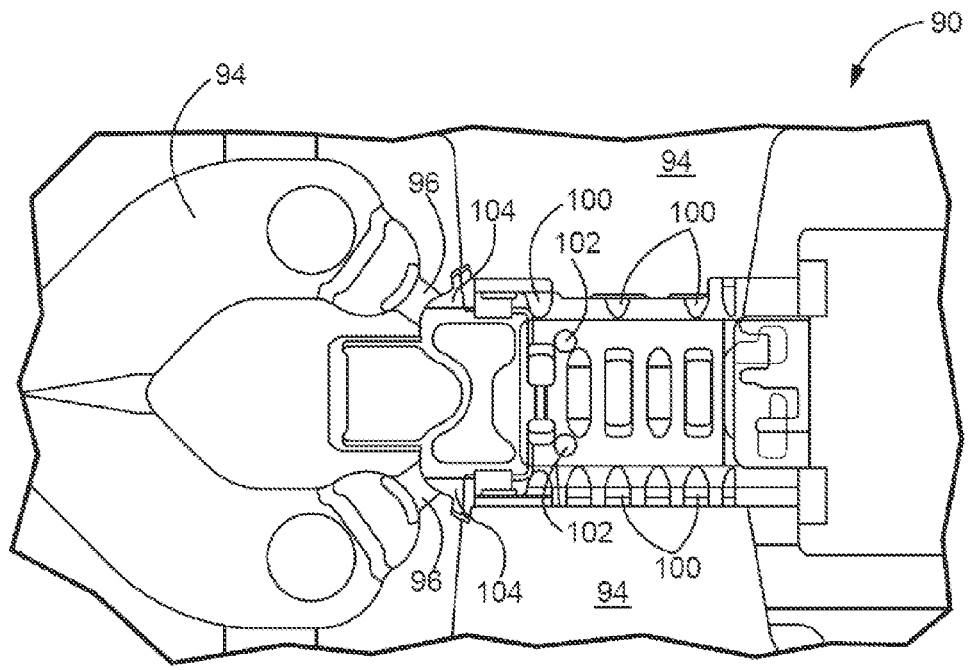
FIG. 14 is a schematic diagram illustrating a first-shot mold which defines features configured to create interaction features on the first-shot assembly.

FIG. 14 is a schematic diagram illustrating first-shot mold 90, which defines divots configured to create protrusions on first-shot assembly 66. For example, in the example illustrated in FIG. 14, first-shot mold 90 includes divots 102 configured to create protrusions 70A, 70B on first-shot assembly 66 and divots 104 configured to create protrusions 72A, 72B on first-shot assembly 66. As described above, the protrusions 70A, 70B may be configured to interact in a particular manner with the second-shot mold during the second step of the two-shot molding process and the protrusions 72A, 72B may be configured to interact in a particular manner with molding material during the second step of the two-shot molding process.

As illustrated in FIG. 14, first-shot mold 90 may define divots 102 configured to receive molding material to create protrusions 70A, 70B on first-shot assembly 66. Divots 102 may be defined within first-shot mold 90 proximate to a side of pre-molding assembly 64 opposite electrode 42. In the examples described herein, divots 102 are positioned proximate to a side of pre-molding assembly 64 that includes antenna loading structure 58 (which is positioned opposite electrode 42 in the examples described herein).

As illustrated in FIG. 14, first-shot mold 90 may also define divots 104 configured to receive molding material to create protrusions 72A, 72B on first-shot assembly 66. Divots 104 may be defined within first-shot mold 90 proximate to a substantially top portion of pre-molding assembly 64. In particular, divots 104 may be defined within first-shot mold 90 such that, when pre-molding assembly 64 is positioned within first-shot mold 90, divots 104 extend between electrode 42 and antenna loading structure 58. In this way, when molding material fills divots 104 during a first-shot molding step, protrusions 72A, 72B may be created on a substantially top portion of first-shot assembly 66. As discussed above, protrusions 72A, 72B may be configured in a particular manner to guide flow of molding material from a substantially top portion of first-shot assembly 66 to a substantially bottom portion of first-shot assembly 66 within a second shot mold. Divots 104 of first-shot mold 90 may reflect a desired configuration of protrusions 72A, 72B, e.g., may define a particular shape, texture, or other characteristics reflective of function of guiding flow of the molding material during the second molding step.

Figure 15:
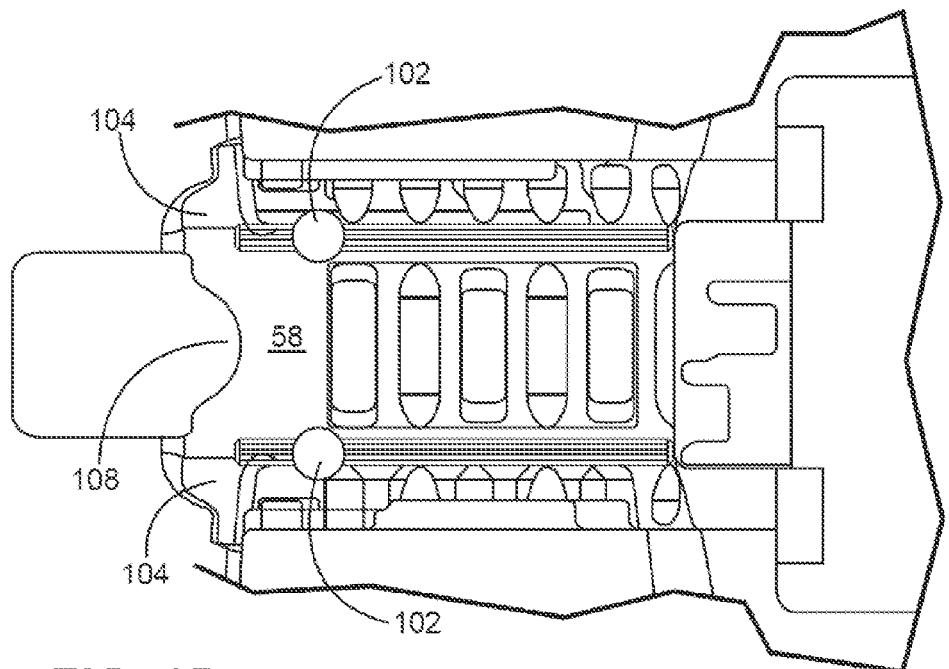
FIG. 15 is a schematic diagram illustrating the pre-molding assembly positioned within the first-shot mold.

FIG. 15 is another schematic diagram illustrating pre-molding assembly 64 positioned within first-shot mold 90. As illustrated in FIG. 15, portion 102 comprises feature 108. Feature 108 may be configured to create suture-hole groove 69 on first-shot assembly 66. For example, molding material may form to the shape of feature 108 proximate to antenna loading structure 58 and electrode 42 to create the indentations suture-hole groove 69.

In addition, divots 102 and 104 are also visible in the schematic of FIG. 15, proximate to antenna loading structure 58. Divots 102 are configured to receive molding material during the first molding step to create protrusions 70A, 70B on the surface of first-shot assembly 66 proximate to antenna loading structure 58 and opposite electrode 42. Divots 104 are configured to receive molding material during the first molding step to create protrusions 72A, 72B extending outward from a substantially top portion of the first-shot assembly 66. During the first molding step, molding material may fill divots 102 and 104 and, upon hardening, may create the protrusions 70A, 70B and 72A, 72B on the first-shot assembly 66.

Figure 16A:
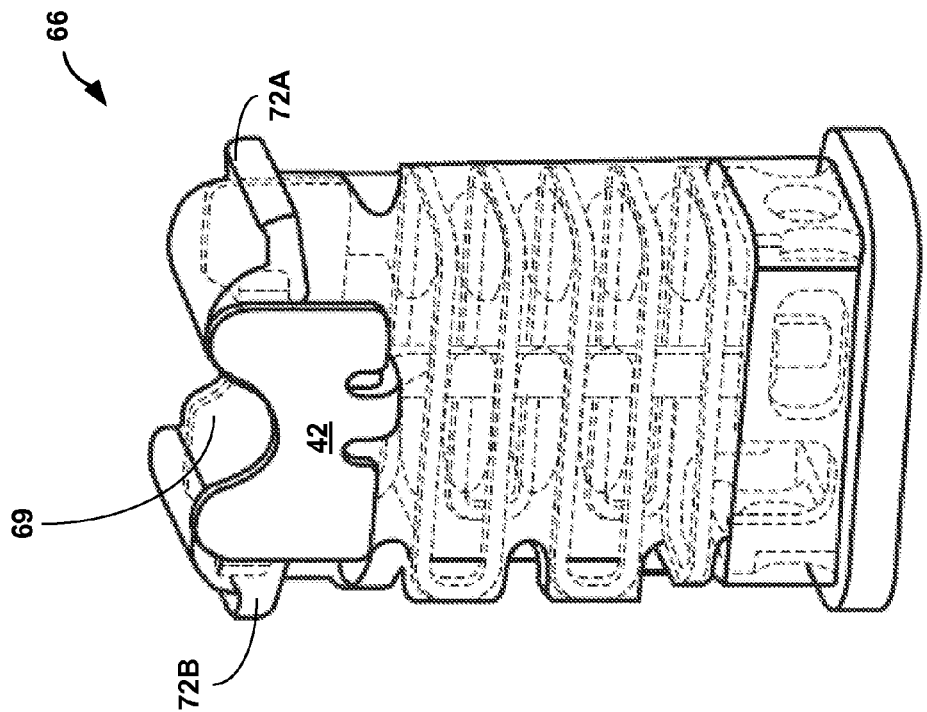
FIGS. 16A and 16B are schematic diagrams illustrating the first-shot assembly after the first-shot assembly has been removed from the first-shot mold.
Figure 16B:
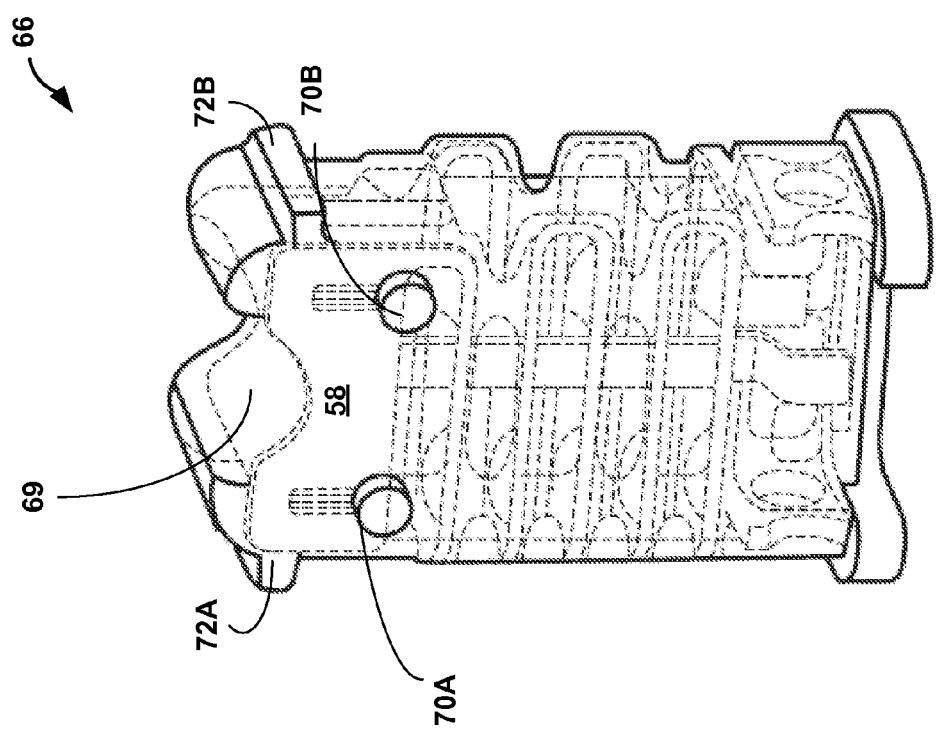

FIGS. 16A and 16B illustrate first-shot assembly 66 after the first molding material has been injected into the first-shot mold 90, the first molding material has been cured/hardened, and the first-shot assembly 66 has been removed from the first-shot mold 90. As shown in FIGS. 16A and 16B, first-shot assembly 66 defines protrusions 70A, 70B and 72A, 72B and suture-hole groove 69. As illustrated, protrusions 70A, 70B extend from a surface of first-shot assembly 66 that is opposite electrode 42, and protrusions 72A, 72B extend outward from a substantially top portion of first-shot assembly 66. As discussed above, protrusions 70A, 70B facilitate keeping electrode 42 free of molding material (e.g., "flash free") during a second molding step, and protrusions 72A, 72B are configured to guide flow of molding material during the second molding step.

Figure 17:
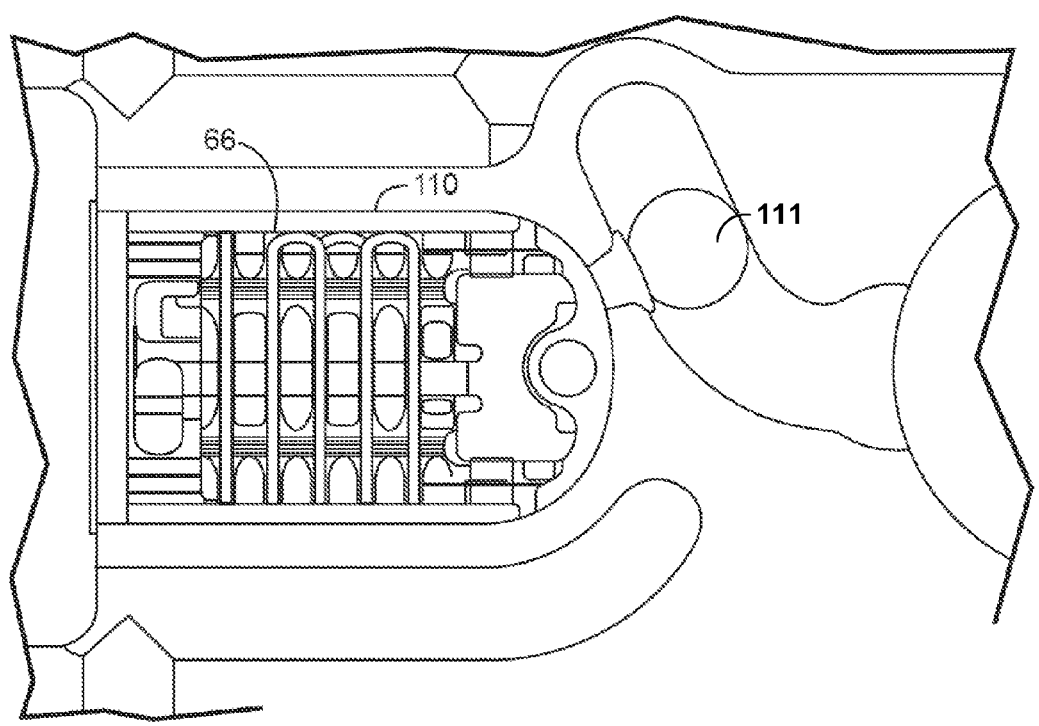
FIG. 17 is a schematic diagram illustrating a first-shot assembly positioned within a second-shot mold.

FIG. 17 is a schematic diagram illustrating first-shot assembly 66 positioned within second-shot mold 110. First-shot assembly 66 may be removed from first-shot mold 90 after the first molding step is complete, and may be subsequently positioned into second-shot mold 110 for a second molding step, as shown in FIG. 17. In some examples, the second molding step may be considered an "overmold" step in that the second step may provide a second layer of molding material over at least part of the first-shot assembly to complete header 38. As illustrated in FIG. 17, second-shot mold 110 is coupled to distributor 111, which is configured to distribute molding material into the cavity of second shot mold 110 during the second molding step.

Figure 18:
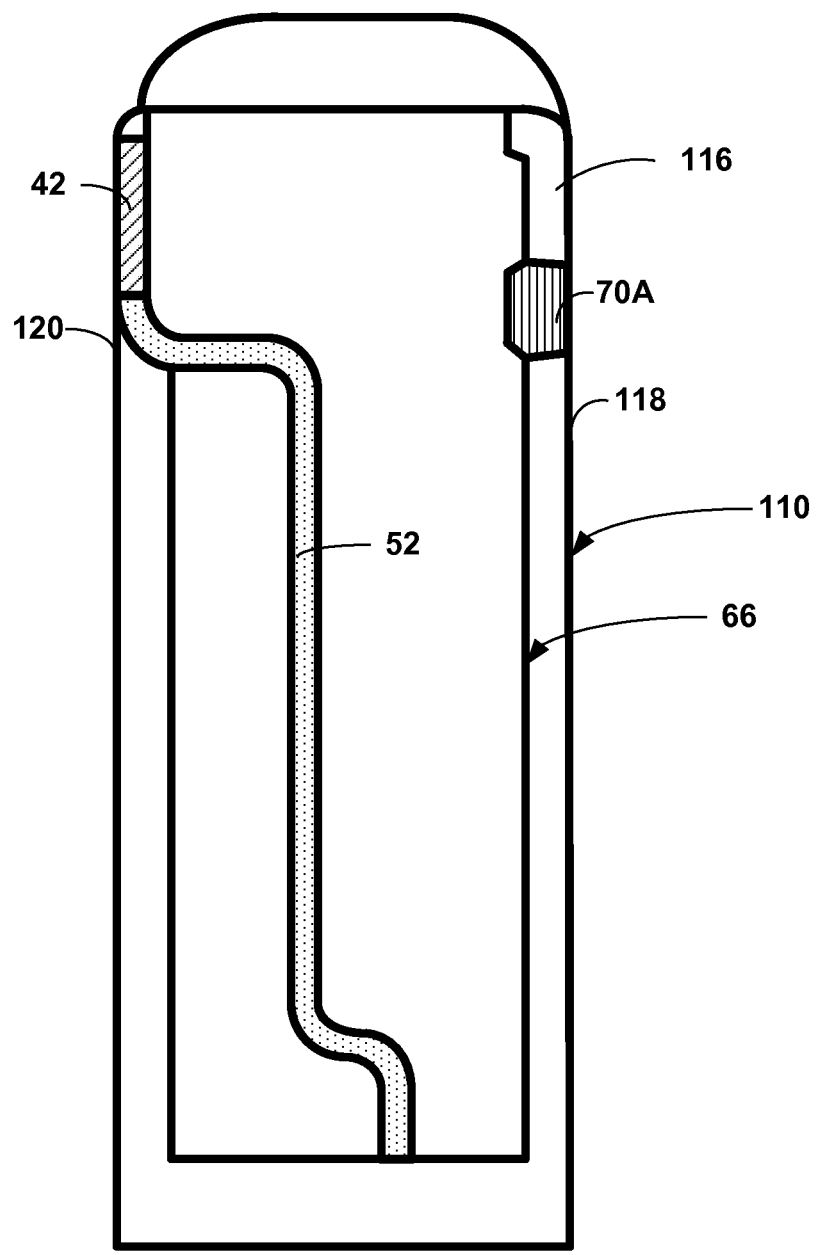
FIG. 18 is a schematic cross-sectional diagram of the first-shot assembly, including the electrode and a protrusion of the first-shot assembly, positioned within a second-shot mold cavity.

FIG. 18 is a schematic cross-sectional diagram of first-shot assembly 66, including electrode 42, shaft 52, and protrusion 70A (protrusion 70B is not shown in the cross-section of FIG. 18), positioned within second-shot mold cavity 116 defined within second-shot mold 110. Antenna 44 is not shown in the cross-section of FIG. 18, for purposes of clarity. In the example illustrated in FIG. 18, second-shot mold 110 includes opposing walls 118 and 120 (e.g., walls 118 and 120 may be considered opposite one another). Wall 118 may also be characterized as being proximate to protrusions 70A, 70B and opposite (e.g., on an opposite side of mold 116) electrode 42; similarly, wall 120 may be characterized as being proximately to electrode 42 and opposite protrusions 70A, 70B. As illustrated in FIG. 16A, protrusions 70A, 70B (70B not shown in the cross-section of FIG. 18) are configured to engage with wall 118 to substantially press electrode 42 against wall 120. In this way, molding material may be prevented from covering electrode 42 because there is no space between electrode 42 and wall 120 into which molding material can enter. Because electrode 42 is pressed against wall 120, electrode 42 may not be covered with molding material during injection of molding material into second-shot mold cavity 116, thus keeping electrode 42 free of molding material, or "flash free." Upon completion of header 38, an outer surface of electrode 42 may be clear and able to sense physiological signals and/or deliver therapy.

Figure 19:
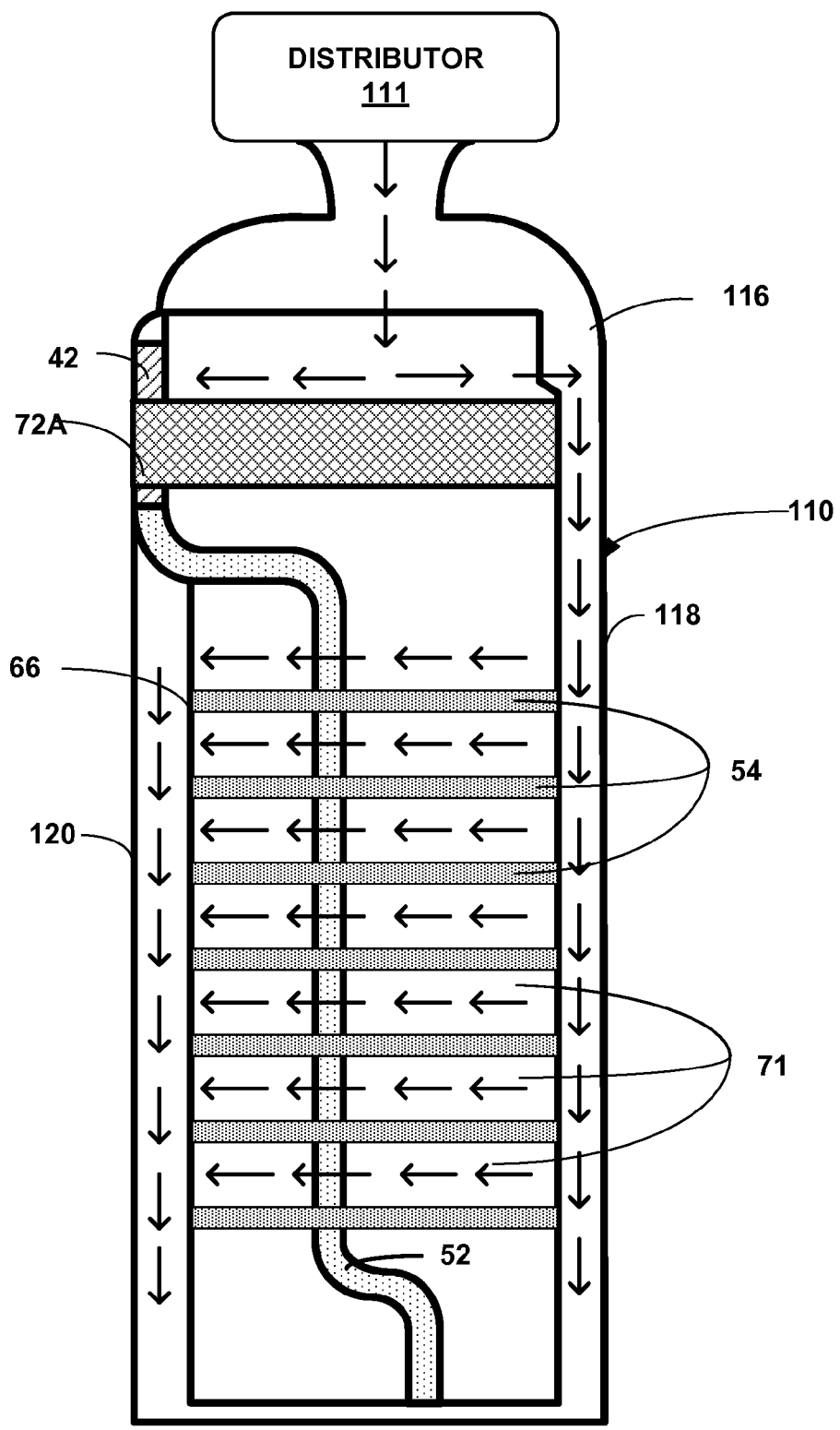
FIG. 19 is a schematic cross-sectional diagram of the first-shot assembly, including a protrusion of the first-shot assembly, positioned within a second-shot mold cavity

FIG. 19 is another cross-sectional schematic diagram of first-shot assembly 66 positioned within second-shot mold cavity 116. FIG. 19 illustrates protrusion 72A, which is configured to guide the flow of molding material during the second molding step. (Protrusion 72B is not visible in the cross section of FIG. 19.) The arrows shown in FIG. 19 illustrate the flow of molding material after it is introduced into second-shot mold cavity 116 through distributor 111.

In the example illustrated in FIG. 19, protrusion 72A extends between electrode 42 and antenna coupling structure 58 (not shown). Protrusion 72A is configured to engage with wall 120 of second-shot mold 110 and a wall of second-shot mold 110 that is substantially perpendicular to wall 120 and substantially parallel to the page of FIG. 19. In this way, protrusion 72A may substantially create a seal such that molding material is initially prevented from flowing along or proximate to wall 120 from the first end of mold cavity 116 proximate to the distributor 11 to the second end of mold cavity 116. That is, protrusion 72A substantially blocks the molding material exiting distributor 111 from traveling along wall 120 initially. Protrusion 72A may substantially force the molding material to instead travel along wall 118 and move over to travel along wall 120 within regions 71 (between segments 54 of antenna 44), instead of initially traveling along wall 120 when it is introduced into mold cavity 116.

In the example illustrated in FIG. 19, molding material travels from distributor 111 into a first end or portion of mold cavity 116, travels along protrusion 72A toward wall 118, and travels downward within mold cavity 116 between wall 118 and a surface of first-shot assembly 66 proximate to antenna loading structure and opposite electrode 42. The molding material then travels toward wall 120 of mold cavity 116 through regions 71 in a single direction (e.g., toward wall 120). The molding material may then travel from a first end of cavity 116 proximate to distributor 111 to a second end of cavity 116 away from distributor 111 along both walls 120 and 118.

The configuration illustrated in FIG. 19 may have one or more advantages. For example, protrusion 72A may force molding material to travel in only one direction within regions 71 because molding material is entering the cavity only along wall 118, which may prevent the creation of air bubbles within the molding material within regions 71. For example, if the molding material were to enter regions 71 from two directions (e.g., moving toward wall 118 and toward wall 120) such that the fronts of molding material would meet substantially in the middle of regions 71, air may be trapped and air bubbles may be created at the location where the two fronts meet. Air bubbles in the molding material may, in some examples, create regions in which the molding material is more fragile, less structurally sound, etc. Thus, protrusions 72A, 72B configured to guide the flow of molding material in the manner illustrated in FIG. 19 may prevent entrapment of air bubbles in the molding material of header 38.

Figure 20B:
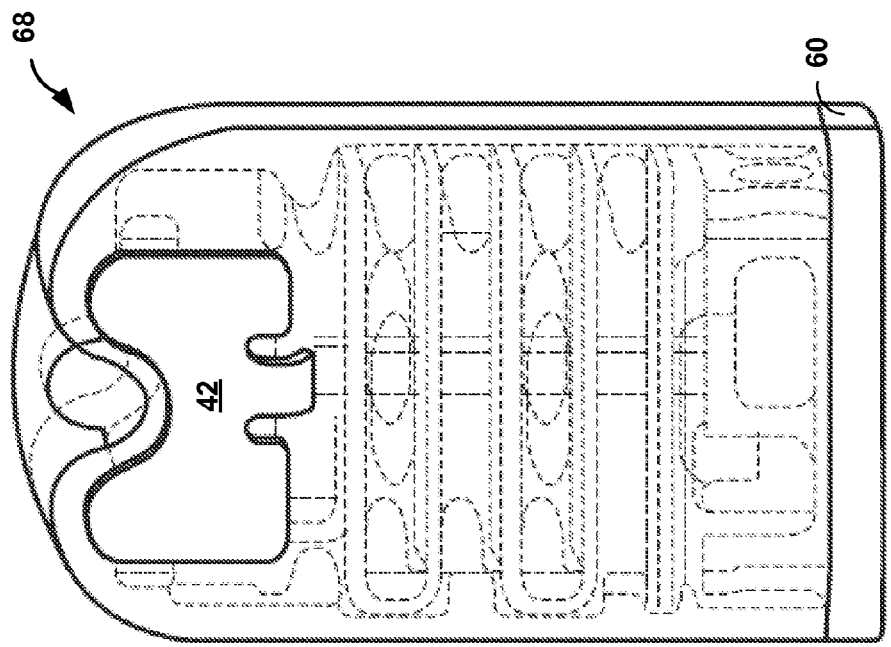
FIGS. 20A and 20B are schematic diagrams illustrating a second-shot assembly after the second-shot assembly has been removed from the second-shot mold.
Figure 20A:
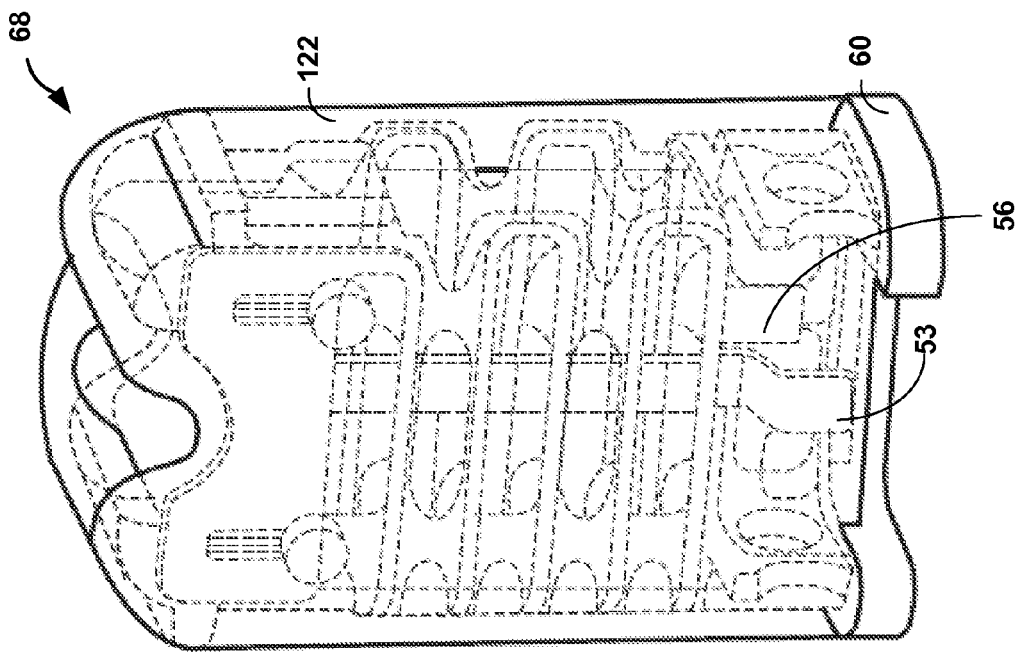

FIGS. 20A, 20B illustrate second-shot assembly 68, or header 38, after assembly 68 has been removed from the second-shot mold 110 (after the second molding step). As illustrated, second-shot assembly 68 includes overmold 122, which may be a layer of cured molding material, over the first-shot assembly 66. As shown in FIG. 20A, distal end 53 of shaft 52 and antenna coupling structure 56 are exposed and free of molding material in assembly 68. Thus, distal end 53 and structure 56 may be electrically coupled to feedthrough wires of body 40 of IMD 16 to facilitate transmission of electrical signals between header 38 and body 40 (e.g., electrical circuitry 48 of body 40). In addition, as shown in FIGS. 20A, 20B, base 60 of attachment plate 46 may also be exposed and free of molding material such that base 60 may be mechanically coupled (e.g., laser welded) to body 40 of IMD 16. As shown in FIG. 20B, electrode 42 is also exposed and free of molding material in assembly 68, such that electrode 42 may sense physiological signals and/or deliver electrical stimulation therapy to patient 14.

Figure 21:
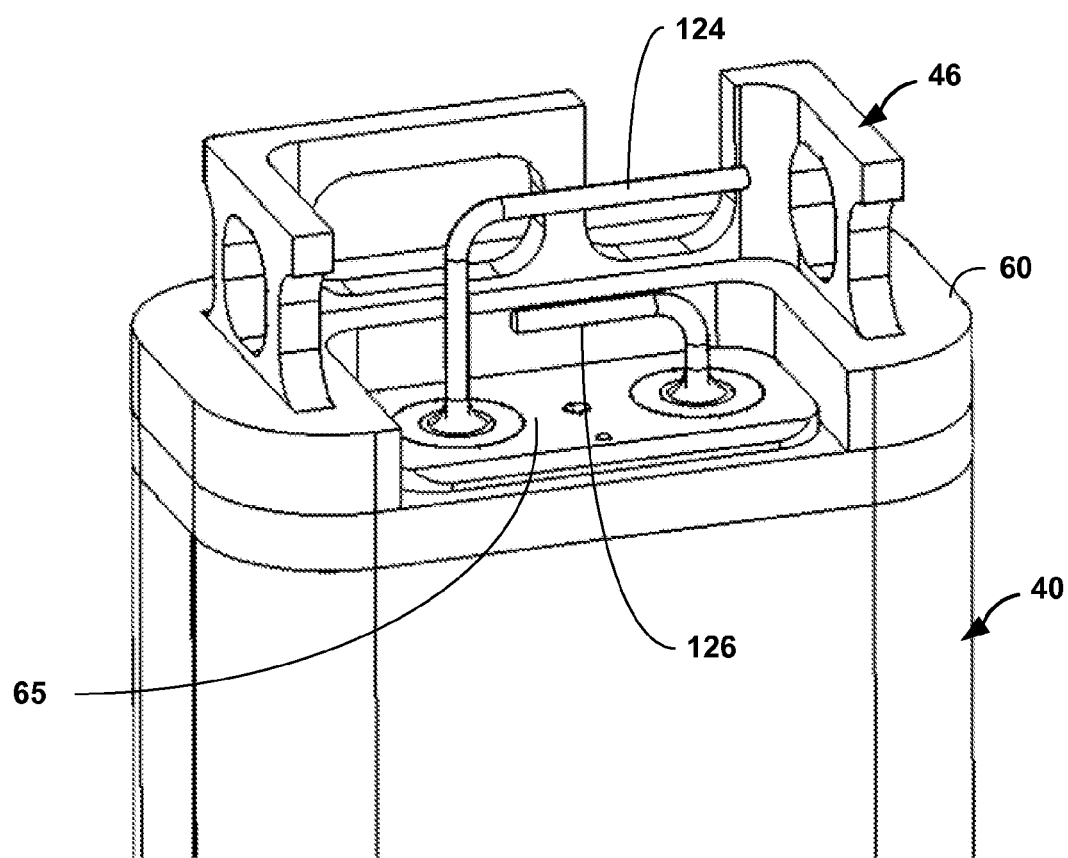
FIG. 21 is a schematic diagram illustrating an attachment plate of a header mechanically coupled to a body of an IMD.

FIG. 21 is a schematic diagram illustrating attachment plate 46 coupled to body 40 of IMD 16. In the diagram shown in FIG. 21, other components of header 38 are not included, for clarity of illustration; however, header 38 as a whole may be mechanically and electrically coupled to body 40 of IMD 16.

As illustrated in FIG. 21, base 60 of attachment plate 46 may be mechanically coupled to body 40. For example, base 60 of attachment plate 46 may be laser welded to body 40 of IMD 16 to mechanically coupled header 38 to body 40. In other examples, base 60 of attachment plate 46 may be mechanically coupled to body 40 using another suitable technique.

As shown in FIG. 21, space 65 (FIGS. 5A, 5D) defined within base 60 of attachment plate 46 is configured to accommodate or receive feedthrough wires 124 and 126 which extend upward into space 65 from body 40. Feedthrough wires 124 and 126 may extend to electrical circuitry within body 40, e.g., electrical circuitry 48, and may be configured to be electrically coupled to antenna 44 and electrode 42, respectively. For example, feedthrough wire 124 may be electrically coupled to antenna coupling structure 56 in order to facilitate communications of IMD 16 via antenna 44, e.g., with programmer 24. Similarly, feedthrough wire 126 may be electrically coupled to distal end 53 of shaft 52 (which extends to electrode 42) in order to facilitate control of electrode 42, e.g., sensing and/or therapy delivery, by a component of body 40, such as a processor. In this way, header 38 (or second-shot assembly 68) may be mechanically and electrically coupled to body 40 of IMD 16.

Figure 22:
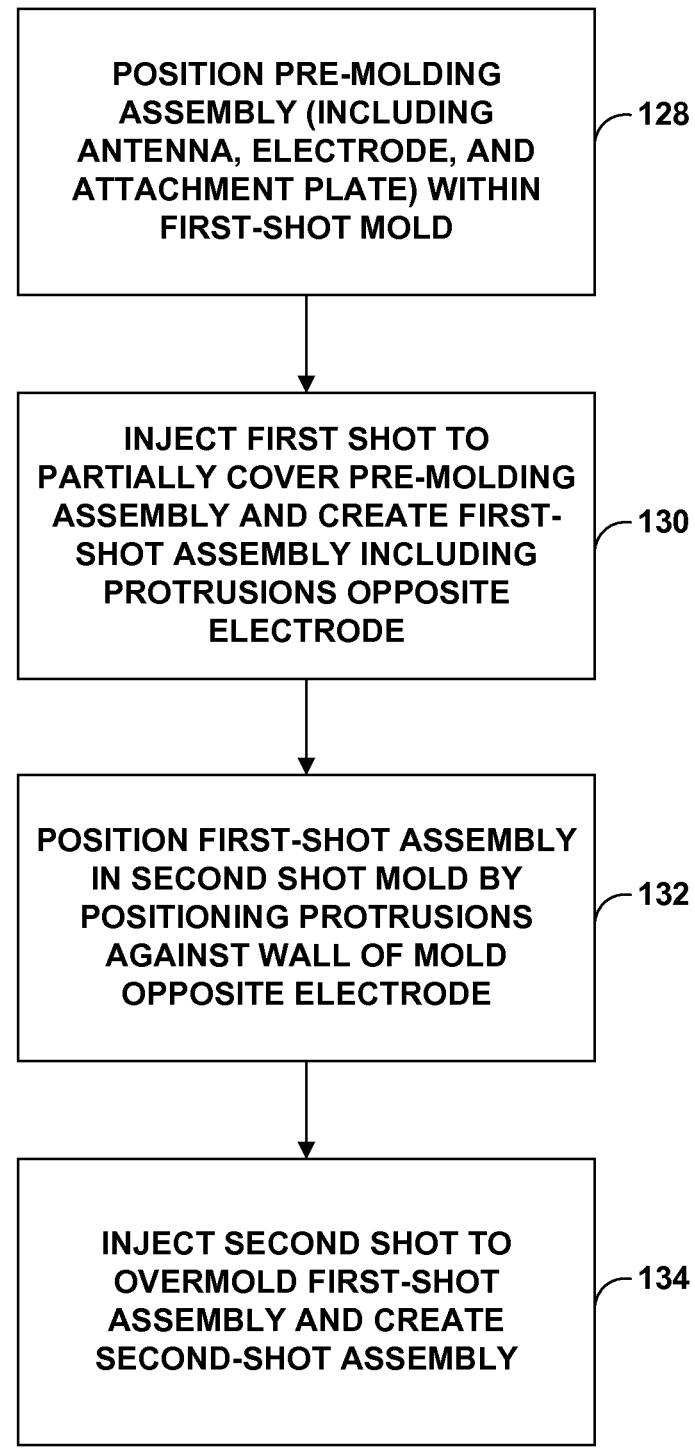
FIG. 22 is a flow diagram illustrating an example technique for creating a header via a two-shot molding process.

FIG. 22 is a flow diagram illustrating an example technique for creating header 38 that includes creating a first-shot assembly with one or more protrusions configured to engage with a wall of a second-shot mold opposite electrode 42 during a second molding step of a two-shot molding process. According to the technique of FIG. 22, pre-molding assembly 64 may be positioned within first-shot mold 90 (128). In some examples, as described above with respect to FIGS. 8-11, a loading fixture, e.g., loading fixture 82, may be utilized to align and transfer pre-molding assembly 64 to first-shot mold 90.

In some examples, first-shot mold 90 may include divots 102 (FIGS. 14, 15) configured to form protrusions 70A, 70B on first-shot assembly 66 after the first molding step. Thus, positioning of pre-molding assembly 64 within first-shot mold 90 may, in some examples, include aligning pre-molding assembly 64 within first-shot mold 90 such that divots 102 are positioned proximate to a particular portion of pre-molding assembly 64, e.g., proximate to a surface of pre-molding assembly 64 opposite electrode 42, such as proximate to antenna loading structure 58, in the examples described herein.

After positioning of pre-molding assembly 64 within first-shot mold 90, a first shot of molding material may be injected into first-shot mold 90 to at least partially cover pre-molding assembly 64 and to create protrusions 70A, 70B on first-shot assembly 66 (130). After the first-shot molding material has been cured and/or hardened, the first-shot assembly 66 may be removed from the first-shot mold and transferred to a second-shot mold 110. In some examples, the first-shot assembly 66 may be transferred to second-shot mold 110 via a second loading fixture.

First-shot assembly 66 may be positioned within second-shot mold 110. In particular, according to the example technique of FIG. 22, first shot assembly 66 may be placed within first-shot mold 90 by placing protrusions 70A, 70B against wall 118 (FIG. 18) of second-shot mold 110, which is opposite electrode 42 (132). In this configuration, protrusions 70A, 70B press against wall 118 and, thus, apply pressure to electrode 42 to press electrode 42 against wall 120. In this way, molding material is prevented from covering electrode 42 and, thus, electrode 42 remains clean.

After first-shot assembly 66 is placed in second-shot mold 110, a second-shot of molding material is injected into second-shot mold 110 to substantially overmold the first-shot assembly 66 and create second-shot assembly 68 (134). In some examples, particular components of second-shot assembly 68 may not be overmolded (e.g., may be kept free of molding material). For example, as described above, in some examples, electrode 42, distal end 53 of shaft 52, antenna coupling structure 58, and/or base 60 of attachment plate 46 may be kept clean and free of molding material.

Figure 23:
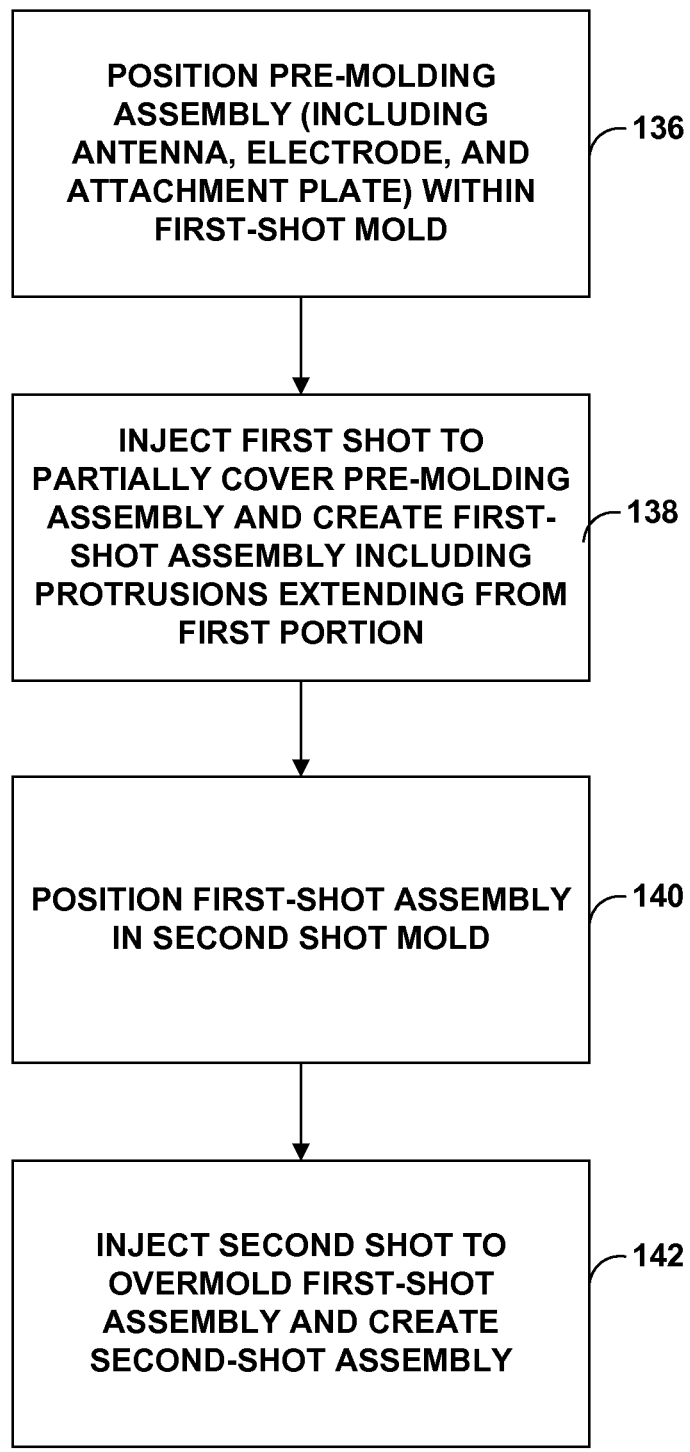
FIG. 23 is a flow diagram illustrating another example technique for creating a header via a two-shot molding process.

FIG. 23 is a flow diagram illustrating an example technique for creating header 38 that includes creating a first-shot assembly with one or more protrusions extending outward from a substantially top portion of the first-shot assembly 66 and configured to guide flow of the second-shot molding material during the second molding step along a surface of the first-shot assembly 66 toward a substantially bottom portion of the first-shot assembly 66 within second-shot mold 110. According to the technique of FIG. 23, pre-molding assembly 64 may be positioned within first-shot mold 90 (136). In some examples, as described above with respect to FIGS. 8-11, a loading fixture, e.g., loading fixture 82, may be utilized to align and transfer pre-molding assembly 64 to first-shot mold 90.

In some examples, first-shot mold 90 may include divots 104 (FIGS. 14, 15) configured to form protrusions 72A, 72B on first-shot assembly 66 after the first molding step. Thus, positioning of pre-molding assembly 64 within first-shot mold 90 may, in some examples, include aligning pre-molding assembly 64 within first-shot mold 90 such that divots 104 are positioned proximate to a particular portion of pre-molding assembly 64, e.g., proximate to a substantially top portion of pre-molding assembly 64, such as proximate to antenna loading structure 58 and electrode 42, in the examples described herein.

After positioning of pre-molding assembly 64 within first-shot mold 90, a first shot of molding material may be injected into first-shot mold 90 to at least partially cover pre-molding assembly 64 and to create protrusions 72A, 72B on a first portion or end of first-shot assembly 66 (138). After the first-shot molding material has been cured and/or hardened, the first-shot assembly 66 may be removed from the first-shot mold and transferred to a second-shot mold 110. In some examples, the first-shot assembly 66 may be transferred to second-shot mold 110 via a second loading fixture.

First-shot assembly 66 may subsequently be positioned within second-shot mold 110 (140). In some examples, as discussed above, first shot assembly 66 may be include protrusions 72A, 72B, which are located on a substantially first end or portion of first-shot assembly 66, where the protrusions 72A, 72B are configured to guide flow of a second-shot molding material that is introduced proximate to the first portion or end of the first shot assembly in the second-shot mold 110. In such examples, when first shot assembly 66 is placed in the second shot mold, protrusions 72A, 72B may be located relatively close to an entry point of molding material into a cavity of second-shot mold 110, in comparison to other portions of second-shot mold 110. In this way, the molding material may contact protrusions 72A, 72B relatively early in its transit through second-shot mold 110 and protrusions 72A, 72B may guide or direct flow of the molding material in a particular manner through the cavity of the second-shot mold from a first end or portion to a second, different end or portion.

After first-shot assembly 66 is placed in second-shot mold 110, a second-shot of molding material is injected into second-shot mold 110 to substantially overmold the first-shot assembly 66 and create second-shot assembly 68 (142). In some examples, particular components of second-shot assembly 68 may not be overmolded (e.g., may be kept free of molding material). For example, as described above, in some examples, electrode 42, distal end 53 of shaft 52, antenna coupling structure 58, and/or base 60 of attachment plate 46 may be kept clean and free of molding material. As mentioned, protrusions 72A, 72B may be configured to guide the second shot of molding material through the cavity of second-shot mold 110 in a particular manner, e.g., by directing molding material through open regions 71 by guiding the molding material around the top portion and down the side of first-shot assembly 66.

Figure 24:
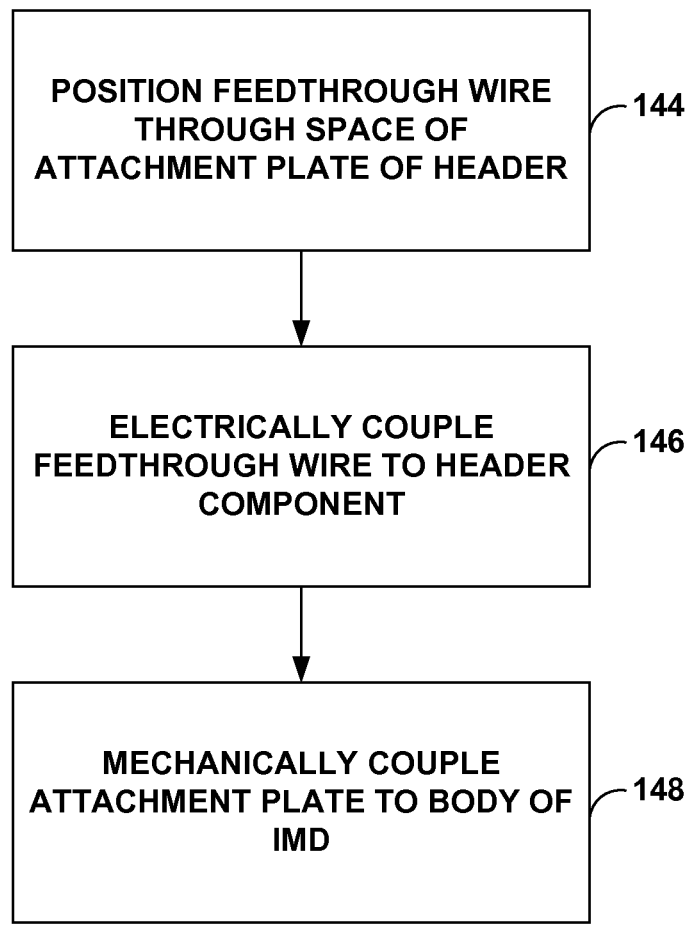
FIG. 24 is a flow diagram illustrating an example technique for coupling a header to a body of an implantable medical device.

FIG. 24 is a flow diagram illustrating an example technique for coupling header 38 to body 40 of IMD 16. Header 38 may, in some examples, be formed via the two step molding processes described herein. Header 38 may be formed to include a header body portion that includes molding material and at least one component within the molding material. In some examples, the header body portion may include some or all components of header 38 other than attachment plate 46. Header 38 may also be formed to include attachment plate 46 that includes base 60 defining space 65, and one or more extensions 62 defining one or more voids 63. As described above, voids 63 may be configured to receive molding material to mechanically couple attachment plate 46 to the other components of header 38, e.g., to the header body.

According to the technique of FIG. 24, feedthrough wires 124 and/or 126 may be positioned through a space defined within attachment plate 46 of header 38 (144). For example, as shown in FIG. 21, feedthrough wires 124 and 126 may be positioned through space 65 defined within base 60 of attachment plate 46 of header 38. In this way, feedthrough wires 124 and 126, which may be electrically coupled to electrical components within body 40 (e.g., electrical circuitry 48 and/or power source 50), may be appropriately positioned to be coupled to components of header 38. Although the examples described herein include two feedthrough wires 124 and 126, in other examples, IMD 16 may include any suitable number of feedthrough wires configured to electrically couple component(s) of body 40 to component(s) of header 38.

According to the technique of FIG. 24, feedthrough wires 124 and/or 126 may be electrically coupled to a component of header 38, e.g., electrode 42 and/or antenna 44 of header 38 (146). For example, feedthrough wire 124 may be electrically coupled to antenna coupling structure 56 of antenna 44, in order to electrically couple components of body 40 of IMD 16 (e.g., electrical circuitry 48 and/or power source 50) to antenna 44. As another example, feedthrough wire 126 may be electrically coupled to distal end 53 of shaft 52, which extends to electrode 42, in order to electrically couple electrode 42 to components of body 40 of IMD 16 (e.g., electrical circuitry 48 and/or power source 50). In this way, one or more components of header 38 may be in electrical communication with components of body 40.

According to the technique of FIG. 24, attachment plate 46 may be mechanically coupled to body 40 of IMD 16 (148). In this way, header 38 and body 40 may be physically integrated to form IMD 16. Attachment plate 46 may be mechanically coupled to body 40 in any suitable manner. For example, base 60 of attachment plate 46 may be laser welded to a portion of body 40, e.g., a portion of body 40 from which feedthrough wires 124 and 126 extend. In other examples, attachment plate 46 may be mechanically coupled to body 40 via another suitable technique.

Various examples have been described. These and other examples are within the scope of the following claims.

The invention claimed is:

1. A header configured to be coupled to a body of an implantable medical device, the header comprising:
   a header body comprising molding material and at least one component within the molding material; and
   an attachment plate configured to couple the header to the body of the implantable medical device, wherein the attachment plate comprises:
      a metal base configured to be mechanically coupled to the body of the implantable medical device, wherein the base defines a space configured to receive at least one feedthrough wire from the body of the implantable medical device, the at least one feedthrough wire configured to be coupled to the at least one component of the header body; and
      at least one extension extending from the base of the attachment plate, wherein the at least one extension defines at least one through hole configured to receive a portion of the molding material to couple the attachment plate to the header body,
   wherein the at least one extension is substantially embedded in the molding material,
   wherein the portion of the molding material is within the through hole such that the attachment plate is mechanically coupled to the header body,
   wherein a portion of the metal base is free of the molding material to facilitate mechanically coupling the header to the body of the implantable medical device by welding the metal base to a metal housing of the body of the implantable medical device.

2. The header of claim 1, wherein the at least one component comprises at least one of an electrode or an antenna.

3. The header of claim 1, wherein the at least one extension is substantially embedded within the molding material.

4. The header of claim 1, wherein the at least one through hole is configured to receive one or more mold cores of a mold during molding of the header.

5. The header of claim 1, wherein the base is configured to be laser welded to the body of the implantable medical device.

6. The header of claim 1, wherein the base of the attachment plate is substantially free of molding material.

7. The header of claim 1, wherein the attachment plate comprises at least one of titanium or a titanium alloy.

8. An implantable medical device comprising:
  a body comprising electrical circuitry enclosed within a metal housing;
  a header coupled to the metal housing, the header comprising:
    a header body comprising molding material and at least one component within the molding material, and
    a metal attachment plate comprising a base that defines a space, and at least one extension extending from the base, wherein the at least one extension defines at least one through hole configured to receive a portion of the molding material to mechanically couple the attachment plate to the header body, wherein the at least one extension is substantially embedded in the molding material, wherein the portion of the molding material is within the through hole such that the attachment plate is mechanically coupled to the header body;
  a weld mechanically coupling the attachment plate to the metal housing of the body, wherein the weld is free of the molding material as the weld is separated from the molding material by the attachment plate; and
  a feedthrough wire configured to be positioned through the space defined by the base of the attachment plate, wherein the feedthrough wire is configured to electrically couple the electrical circuitry and the at least one component of the header body, and
  wherein the base of the attachment plate is configured to mechanically couple to the body of the implantable medical device.

9. The set of claim 8, wherein the at least one component comprises an electrode, and wherein the header body further comprises a shaft coupled to the electrode, wherein the feedthrough wire is configured to electrically couple a distal end of the shaft to the electrical circuitry.

10. The set of claim 8, wherein the at least one component comprises an antenna comprising an antenna coupling structure, wherein the feedthrough wire is configured to electrically couple the antenna coupling structure to the electrical circuitry.

11. The set of claim 8, wherein the base of the attachment plate is laser welded to the body of the implantable medical device.

12. A method comprising:
  forming a header for an implantable medical device, wherein the header comprises:
    a header body comprising molding material and at least one component within the molding material, and
    an attachment plate comprising a base that defines a space, and at least one extension extending from the base, wherein the at least one extension defines at least one through hole configured to receive a portion of the molding material to mechanically couple the attachment plate to the header body, wherein the at least one extension is substantially embedded in the molding material, wherein the portion of the molding material is within the through hole such that the attachment plate is mechanically coupled to the header body;
  positioning at least one feedthrough wire through the space defined by the base of the attachment plate;
  electrically coupling the at least one feedthrough wire to the component of the header; and
  after forming the header with the attachment plate mechanically coupled to the header body, mechanically coupling the base of the attachment plate to a body of the implantable medical device,
  wherein the at least one feedthrough wire is configured to electrically couple electrical circuitry of the body of the implantable medical device to the component of the header.

13. The method of claim 12, wherein mechanically coupling the base of the attachment plate to the body of the implantable medical device comprises laser welding the base of the attachment plate to the body of the implantable medical device.

14. The method of claim 12, wherein forming a header for an implantable medical device comprises forming the header via a two step molding process.

15. The method of claim 12, wherein the at least one component comprises an electrode, and wherein the header body further comprises a shaft coupled to the electrode, wherein electrically coupling the at least one feedthrough wire to the component of the header comprises electrically coupling the at least one feedthrough wire to a distal end of the shaft.

16. The method of claim 12, wherein the at least one component comprises an antenna comprising an antenna coupling structure, wherein electrically coupling the at least one feedthrough wire to the component of the header comprises electrically coupling the at least one feedthrough wire to the antenna coupling structure.

17. The method of claim 12, wherein forming the header for the implantable medical device comprises:
  positioning the at least one component of the header and the attachment plate of the header within a first mold, wherein the molding material includes a first shot molding material and a second shot molding material, injecting the first shot molding material into the first mold in a manner that secures the at least one component and the attachment plate relative to one another while leaving a surface of the attachment plate exposed to create a first-shot assembly, wherein the exposed surface of the attachment plate is configured to be positioned adjacent the body of the implantable medical device,
  positioning the first-shot assembly within a second mold; and
  injecting a second shot molding material into the second mold to create the header, wherein the exposed surface of the attachment plate remains exposed following the injection of the second shot molding material into the second mold to create the header.

18. The method of claim 17, wherein the first shot molding material forms protrusions in the first-shot assembly, wherein positioning the first-shot assembly within the second mold includes positioning the first-shot assembly within the second mold such that the protrusions engage a wall of the second mold to compress the first-shot assembly within the second mold such that an outer surface of first-shot assembly firmly pressed against the wall of the second-shot mold.

19. The method of claim 18,
  wherein the at least one component comprises an electrode, wherein positioning the first-shot assembly within the second mold includes positioning the first-shot assembly within the second mold such that an outer surface of the electrode is firmly pressed against the wall of the second-shot mold, and wherein the outer surface of the electrode remains substantially uncovered by the second shot molding material following the injection of the second shot molding material into the second-shot mold.

20. The method of claim 19, wherein the at least one component comprises an antenna.

* * * * *